(12) United States Patent
Lau et al.

(10) Patent No.: US 7,404,793 B2
(45) Date of Patent: Jul. 29, 2008

(54) HEART FAILURE TREATMENT DEVICE AND METHOD

(75) Inventors: Lilip Lau, Los Altos, CA (US); Anuja Patel, Sunnyvale, CA (US)

(73) Assignee: Paracor Medical, Inc., Sunnyvale, CA (US)

( * ) Notice: Subject to any disclaimer, the term of this patent is extended or adjusted under 35 U.S.C. 154(b) by 805 days.

(21) Appl. No.: 10/837,157

(22) Filed: Apr. 30, 2004

(65) Prior Publication Data

US 2005/0033109 A1 Feb. 10, 2005

(51) Int. Cl.
*A61F 2/00* (2006.01)
(52) U.S. Cl. ........................................................ 600/37
(58) Field of Classification Search ............. 600/16–18, 600/37; 128/897, 898; 606/193, 195, 202, 606/204
See application file for complete search history.

(56) References Cited

U.S. PATENT DOCUMENTS

| | | | |
|---|---|---|---|
| 2,278,926 A | 4/1942 | Hartwell |
| 2,826,193 A | 3/1958 | Vineberg |
| 3,464,322 A | 9/1969 | Pequignot |
| 3,513,836 A | 5/1970 | Sausse |
| 3,587,567 A | 6/1971 | Schiff |
| 3,613,672 A | 10/1971 | Schiff |
| 3,966,401 A | 6/1976 | Hancock et al. |
| 3,983,863 A | 10/1976 | Janke et al. |
| 3,988,782 A | 11/1976 | Dardik et al. |
| 4,011,947 A | 3/1977 | Sawyer |
| 4,048,990 A | 9/1977 | Goetz |
| 4,065,816 A | 1/1978 | Sawyer |
| 4,108,161 A | 8/1978 | Samuels et al. |
| 4,192,293 A | 3/1980 | Asrican |
| 4,211,325 A | 7/1980 | Wright |
| 4,261,342 A | 4/1981 | Aranguren Duo |
| 4,306,318 A | 12/1981 | Mano et al. |
| 4,372,293 A | 2/1983 | Vijil-Rosales |
| 4,403,604 A | 9/1983 | Wilkinson et al. |
| 4,428,375 A | 1/1984 | Ellman |
| 4,512,471 A | 4/1985 | Kaster et al. |
| 4,536,893 A | 8/1985 | Parravicini |

(Continued)

FOREIGN PATENT DOCUMENTS

DE 3831 540 A1 4/1989

(Continued)

OTHER PUBLICATIONS

Wharton, J. Marcus, et al., Electrophysiological Effects of Monophasic and Biphasic Stimuli in Normal and Infarcted Dogs, *PACE*, vol. 13, pp. 1158-1172, Sep. 1990.

(Continued)

*Primary Examiner*—Samuel G Gilbert
(74) *Attorney, Agent, or Firm*—Fulwider Patton LLP

(57) ABSTRACT

A method and apparatus for treating heart failure is configured to be placed about at least a portion of a patient's heart to apply a mild compressive force on the heart over a range of elastic deformation of the apparatus. The apparatus can be shifted to second range of deformation. In some embodiments, the apparatus is shifted to the second range of deformation by application of a stimulus or alteration of environmental conditions beyond a threshold level.

12 Claims, 19 Drawing Sheets

U.S. PATENT DOCUMENTS

| | | |
|---|---|---|
| 4,545,783 A | 10/1985 | Vaughn |
| 4,628,937 A | 12/1986 | Hess et al. |
| 4,630,597 A | 12/1986 | Kantrowitz et al. |
| 4,665,906 A | 5/1987 | Jervis |
| 4,690,134 A | 9/1987 | Snyders |
| 4,697,703 A | 10/1987 | Will |
| 4,750,619 A | 6/1988 | Cohen et al. |
| 4,821,723 A | 4/1989 | Baker, Jr. et al. |
| 4,827,932 A | 5/1989 | Ideker et al. |
| 4,834,707 A | 5/1989 | Evans |
| 4,838,288 A | 6/1989 | Wright et al. |
| 4,840,626 A | 6/1989 | Linsky et al. |
| 4,863,016 A | 9/1989 | Fong et al. |
| 4,878,890 A | 11/1989 | Bilweis |
| 4,936,857 A | 6/1990 | Kulik |
| 4,957,477 A | 9/1990 | Lundback |
| 4,960,424 A | 10/1990 | Grooters |
| 4,973,300 A | 11/1990 | Wright |
| 4,976,730 A | 12/1990 | Kwan-Gett |
| 5,031,762 A | 7/1991 | Heacox |
| 5,057,117 A | 10/1991 | Atweh |
| 5,067,957 A | 11/1991 | Jervis |
| 5,087,243 A | 2/1992 | Avitall |
| 5,098,369 A | 3/1992 | Heilman et al. |
| 5,106,386 A | 4/1992 | Isner et al. |
| 5,119,804 A | 6/1992 | Anstadt |
| 5,131,905 A | 7/1992 | Grooters |
| 5,150,706 A | 9/1992 | Cox et al. |
| 5,169,381 A | 12/1992 | Snyders |
| 5,186,711 A | 2/1993 | Epstein |
| 5,190,546 A | 3/1993 | Jervis |
| 5,192,314 A | 3/1993 | Daskalakis |
| 5,197,978 A | 3/1993 | Hess |
| 5,256,132 A | 10/1993 | Snyders |
| 5,279,539 A | 1/1994 | Bohan et al. |
| 5,290,217 A | 3/1994 | Campos |
| 5,336,254 A | 8/1994 | Brennen et al. |
| 5,344,442 A | 9/1994 | Deac |
| 5,352,184 A | 10/1994 | Goldberg et al. |
| 5,356,432 A | 10/1994 | Rutkow et al. |
| 5,366,460 A | 11/1994 | Eberbach |
| 5,383,840 A | 1/1995 | Heilman et al. |
| 5,385,156 A | 1/1995 | Oliva |
| 5,385,229 A | 1/1995 | Bittmann et al. |
| 5,385,528 A | 1/1995 | Wilk |
| 5,405,360 A | 4/1995 | Tovey |
| 5,429,584 A | 7/1995 | Chiu |
| 5,433,727 A | 7/1995 | Sideris |
| 5,451,234 A * | 9/1995 | Wassermann ............... 606/203 |
| 5,456,711 A | 10/1995 | Hudson |
| 5,460,962 A | 10/1995 | Kemp |
| 5,500,015 A | 3/1996 | Deac |
| 5,507,779 A | 4/1996 | Altman |
| 5,509,428 A | 4/1996 | Dunlop |
| 5,524,633 A | 6/1996 | Heaven et al. |
| 5,533,958 A | 7/1996 | Wilk |
| 5,534,024 A | 7/1996 | Rogers et al. |
| 5,545,210 A | 8/1996 | Hess et al. |
| 5,558,617 A | 9/1996 | Heilman et al. |
| 5,571,215 A | 11/1996 | Sterman et al. |
| 5,582,616 A | 12/1996 | Bolduc et al. |
| 5,584,803 A | 12/1996 | Stevens et al. |
| 5,593,424 A | 1/1997 | Northrup, III |
| 5,593,441 A | 1/1997 | Lichtenstein et al. |
| 5,597,378 A | 1/1997 | Jervis |
| 5,603,337 A | 2/1997 | Jarvik |
| 5,607,477 A | 3/1997 | Schindler et al. |
| 5,647,372 A | 7/1997 | Tovey et al. |
| 5,647,380 A | 7/1997 | Campbell et al. |
| 5,695,525 A | 12/1997 | Mulhauser et al. |
| 5,702,343 A | 12/1997 | Alferness |
| 5,713,954 A | 2/1998 | Rosenberg et al. |
| 5,727,569 A | 3/1998 | Benetti et al. |
| 5,749,839 A | 5/1998 | Kovacs |
| 5,782,746 A | 7/1998 | Wright |
| 5,800,334 A | 9/1998 | Wilk |
| 5,800,528 A | 9/1998 | Lederman et al. |
| 5,814,097 A | 9/1998 | Sterman et al. |
| 5,824,028 A | 10/1998 | Knisley |
| 5,836,311 A | 11/1998 | Borst et al. |
| 5,848,962 A | 12/1998 | Feindt et al. |
| 5,849,005 A | 12/1998 | Garrison et al. |
| 5,853,422 A | 12/1998 | Huebsch et al. |
| 5,865,791 A | 2/1999 | Whayne et al. |
| 5,876,432 A | 3/1999 | Lau et al. |
| 5,904,690 A | 5/1999 | Middleman et al. |
| 5,910,124 A | 6/1999 | Rubin |
| 5,927,284 A | 7/1999 | Borst et al. |
| 5,948,019 A | 9/1999 | Shu et al. |
| 5,957,977 A | 9/1999 | Melvin |
| 5,961,440 A | 10/1999 | Schweich, Jr. et al. |
| 5,976,069 A | 11/1999 | Navia et al. |
| 5,979,456 A | 11/1999 | Magovern |
| 5,984,857 A | 11/1999 | Buck et al. |
| 5,990,378 A | 11/1999 | Ellis |
| 6,007,486 A | 12/1999 | Hunt et al. |
| 6,015,378 A | 1/2000 | Borst et al. |
| 6,024,096 A | 2/2000 | Buckberg |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,076,013 A | 6/2000 | Brennan et al. |
| 6,077,214 A | 6/2000 | Mortier et al. |
| 6,077,218 A | 6/2000 | Alferness |
| 6,079,414 A | 6/2000 | Roth |
| 6,085,754 A | 7/2000 | Alferness et al. |
| 6,095,968 A | 8/2000 | Snyders |
| 6,110,100 A | 8/2000 | Talpade |
| 6,117,159 A | 9/2000 | Huebsch et al. |
| 6,117,979 A | 9/2000 | Hendriks et al. |
| 6,123,662 A | 9/2000 | Alferness et al. |
| 6,125,852 A | 10/2000 | Stevens et al. |
| 6,126,590 A | 10/2000 | Alferness |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,166,184 A | 12/2000 | Hendriks et al. |
| 6,169,922 B1 | 1/2001 | Alferness et al. |
| 6,174,279 B1 | 1/2001 | Girard |
| 6,179,791 B1 | 1/2001 | Krueger |
| 6,183,411 B1 | 2/2001 | Mortier et al. |
| 6,190,408 B1 | 2/2001 | Melvin |
| 6,193,648 B1 | 2/2001 | Krueger |
| 6,206,820 B1 | 3/2001 | Kazi et al. |
| 6,214,047 B1 | 4/2001 | Melvin |
| 6,217,894 B1 | 4/2001 | Sawhney et al. |
| 6,221,103 B1 | 4/2001 | Melvin |
| 6,224,540 B1 | 5/2001 | Ledermann et al. |
| 6,230,714 B1 | 5/2001 | Alferness et al. |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,282,445 B1 | 8/2001 | Reinhardt et al. |
| 6,287,250 B1 | 9/2001 | Peng et al. |
| 6,293,906 B1 | 9/2001 | Vanden Hoek et al. |
| 6,306,141 B1 | 10/2001 | Jervis |
| 6,312,725 B1 | 11/2001 | Wallace et al. |
| 6,352,710 B2 | 3/2002 | Sawhney et al. |
| 6,360,749 B1 | 3/2002 | Jayaraman |

| | | |
|---|---|---|
| 6,375,608 B1 | 4/2002 | Alferness |
| 6,390,976 B1 | 5/2002 | Spence et al. |
| 6,402,679 B1 | 6/2002 | Mortier et al. |
| 6,402,680 B2 | 6/2002 | Mortier et al. |
| 6,406,420 B1 | 6/2002 | McCarthy et al. |
| 6,409,760 B1 | 6/2002 | Melvin |
| 6,416,459 B1 | 7/2002 | Haindl |
| 6,425,856 B1 | 7/2002 | Shapland et al. |
| 6,432,039 B1 | 8/2002 | Wardle |
| 6,451,025 B1 | 9/2002 | Jervis |
| 6,482,146 B1 | 11/2002 | Alferness et al. |
| 6,517,570 B1 | 2/2003 | Lau et al. |
| 6,537,203 B1 | 3/2003 | Alferness et al. |
| 6,544,168 B2 | 4/2003 | Alferness |
| 6,547,821 B1 | 4/2003 | Taylor et al. |
| 6,564,094 B2 | 5/2003 | Alferness et al. |
| 6,567,699 B2 | 5/2003 | Alferness et al. |
| 6,569,082 B1 | 5/2003 | Chin |
| 6,572,533 B1 | 6/2003 | Shapland et al. |
| 6,575,921 B2 | 6/2003 | Vanden Hoek et al. |
| 6,582,355 B2 | 6/2003 | Alferness et al. |
| 6,587,734 B2 | 7/2003 | Okuzumi |
| 6,595,912 B2 | 7/2003 | Lau et al. |
| 6,602,184 B2 | 8/2003 | Lau et al. |
| 6,612,978 B2 | 9/2003 | Lau et al. |
| 6,612,979 B2 | 9/2003 | Lau et al. |
| 6,633,780 B1 | 10/2003 | Berger |
| 6,645,139 B2 | 11/2003 | Haindl |
| 6,663,558 B2 | 12/2003 | Lau et al. |
| 6,673,009 B1 | 1/2004 | Vanden Hoek et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,620 B2 | 2/2004 | Gifford, III et al. |
| 6,685,627 B2 | 2/2004 | Jayaraman |
| 6,689,048 B2 | 2/2004 | Vanden Hoek et al. |
| 6,695,769 B2 | 2/2004 | French et al. |
| 6,699,259 B2 | 3/2004 | Fogarty et al. |
| 6,701,929 B2 | 3/2004 | Hussein |
| 6,702,732 B1 | 3/2004 | Lau et al. |
| 6,723,041 B2 | 4/2004 | Lau et al. |
| 6,730,016 B1 | 5/2004 | Cox et al. |
| 6,755,779 B2 | 6/2004 | Vanden Hoek et al. |
| 6,759,431 B2 | 7/2004 | Hunter et al. |
| 6,818,018 B1 | 11/2004 | Sawhney |
| 6,833,408 B2 | 12/2004 | Sehl et al. |
| 6,876,887 B2 | 4/2005 | Okuzumi |
| 6,881,185 B2 | 4/2005 | Vanden Hoek et al. |
| 6,887,192 B1 | 5/2005 | Whayne et al. |
| 6,893,392 B2 | 5/2005 | Alferness |
| 6,896,652 B2 | 5/2005 | Alferness et al. |
| 6,902,522 B1 | 6/2005 | Walsh et al. |
| 6,902,524 B2 | 6/2005 | Alferness et al. |
| 6,908,426 B2 | 6/2005 | Shapland et al. |
| 2001/0029314 A1 | 10/2001 | Alferness et al. |
| 2001/0047122 A1 | 11/2001 | Vanden Hoek et al. |
| 2002/0007216 A1 | 1/2002 | Melvin |
| 2002/0019580 A1 | 2/2002 | Lau et al. |
| 2002/0022880 A1 | 2/2002 | Melvin |
| 2002/0032364 A1 | 3/2002 | Lau et al. |
| 2002/0068849 A1 | 6/2002 | Schweich, Jr. et al. |
| 2002/0077524 A1 | 6/2002 | Schweich, Jr. et al. |
| 2002/0082647 A1 | 6/2002 | Alferness et al. |
| 2002/0091296 A1 | 7/2002 | Alferness |
| 2002/0103511 A1 | 8/2002 | Alferness et al. |
| 2002/0151950 A1 | 10/2002 | Okuzumi |
| 2003/0060674 A1 | 3/2003 | Gifford, III et al. |
| 2003/0060677 A1 | 3/2003 | French et al. |
| 2003/0060895 A1 | 3/2003 | French et al. |
| 2003/0065248 A1 | 4/2003 | Lau et al. |
| 2003/0199733 A1 | 10/2003 | Shapland et al. |
| 2003/0199955 A1 | 10/2003 | Struble et al. |
| 2003/0229265 A1 | 12/2003 | Girard et al. |
| 2004/0133069 A1 | 7/2004 | Shapland et al. |
| 2004/0147805 A1 | 7/2004 | Lau |
| 2004/0171907 A1 | 9/2004 | Alferness et al. |
| 2004/0171908 A1 | 9/2004 | Alferness et al. |
| 2005/0055032 A1 | 3/2005 | Lau |
| 2005/0059854 A1 | 3/2005 | Hoek et al. |
| 2005/0085688 A1 | 4/2005 | Girard et al. |

FOREIGN PATENT DOCUMENTS

| | | |
|---|---|---|
| DE | 38 31 540 C2 | 6/1993 |
| DE | 295 17 393 U1 | 3/1996 |
| EP | 0 370 931 A1 | 5/1990 |
| EP | 0 280 564 B1 | 6/1993 |
| EP | 0 583 012 B1 | 7/1996 |
| EP | 0 791 330 A3 | 8/1997 |
| EP | 0 919 193 A1 | 6/1999 |
| FR | 2 527 435 | 12/1983 |
| FR | 0 645 739 | 10/1990 |
| GB | 2 115 287 A | 9/1983 |
| GB | 2 209 678 A | 5/1989 |
| JP | 60-203250 | 10/1985 |
| JP | 1-145066 | 6/1989 |
| JP | 1-271829 | 10/1989 |
| SU | 1009457 | 4/1983 |
| SU | 1009457 A | 4/1983 |
| SU | 1734767 A1 | 5/1992 |
| WO | WO 91/19465 | 12/1991 |
| WO | WO 95/06447 | 3/1995 |
| WO | WO 96/04852 | 2/1996 |
| WO | WO 96/40356 | 12/1996 |
| WO | WO 97/20505 | 6/1997 |
| WO | WO 97/24101 | 7/1997 |
| WO | WO 98/03213 | 1/1998 |
| WO | WO 98/14136 | 4/1998 |
| WO | WO 98/26738 | 6/1998 |
| WO | WO 98/29041 | 7/1998 |
| WO | WO 98/58598 | 12/1998 |
| WO | WO 00/02500 | 1/1999 |
| WO | WO 99/11201 | 3/1999 |
| WO | WO 99/30647 | 6/1999 |
| WO | WO 99/44534 | 9/1999 |
| WO | WO 99/44680 | 9/1999 |
| WO | WO 99/53977 | 10/1999 |
| WO | WO 99/56655 | 11/1999 |
| WO | WO 00/02500 | 1/2000 |
| WO | WO 00/06026 | 2/2000 |
| WO | WO 00/06027 | 2/2000 |
| WO | WO 00/06028 | 2/2000 |
| WO | WO 00/060267 | 2/2000 |
| WO | WO 00/13722 | 3/2000 |
| WO | WO 00/16700 | 3/2000 |
| WO | WO 00/18320 | 4/2000 |
| WO | WO 00/28912 | 5/2000 |
| WO | WO 00/28918 | 5/2000 |
| WO | WO 00/36995 | 6/2000 |
| WO | WO/0036995 | 6/2000 |
| WO | WO 00/42919 | 7/2000 |
| WO | WO 00/45735 | 8/2000 |
| WO | WO 00/48795 | 8/2000 |
| WO | WO 00/62727 | 10/2000 |
| WO | WO 99/53977 | 10/2000 |
| WO | WO 00/74769 | 12/2000 |
| WO | WO 01/17437 | 3/2001 |
| WO | WO 01/21098 | 3/2001 |
| WO | WO 01/91667 A2 | 6/2001 |
| WO | WO 01/50981 | 7/2001 |
| WO | WO 01/67985 | 9/2001 |
| WO | WO 01/85061 | 11/2001 |
| WO | WO 01/91667 | 12/2001 |
| WO | WO 01/95830 | 12/2001 |
| WO | WO 01/95831 | 12/2001 |
| WO | WO 01/95832 | 12/2001 |

| WO | WO 02/13726 | 2/2002 |
| WO | WO 02/19917 | 3/2002 |
| WO | WO 03/026483 | 4/2003 |
| WO | WO 03/026484 | 4/2003 |
| WO | WO 03/026485 | 4/2003 |

OTHER PUBLICATIONS

Shabetai, Ralph, The Role of the Pericardium in the Pathophysiology of Heart Failure, Congestive Heart Failure, Second Edition, Chapter 9, pp. 157-187, 2000.

Cohn, Jay N., M.D., The Management of Chronic Heart Failure, The New England Journal of Medicine, vol. 335, No. 7, pp. 490-498, Aug. 15, 1996.

Zhou, Xiaohong, et al., Epicardial Mapping of Ventricular Defibrillation With Monophasic and Biphasic Shocks in Dogs, Circulation Research, vol. 72, No. 1, pp. 145-160, Jan. 1993.

Shorofsky, Stephen R., et al., Comparison of Step-Down and Binary Search Algorithms for Determination of Defibrillation Threshold in Humans, PACE, vol. 27, pp. 218-220, Feb. 2004.

Gold, Michael R., M.D., et al., Comparison of Single- and Dual-Coil Active Pectoral Defibrillation Lead Systems, Journal of the American College of Cardiology, vol. 31, No. 6, pp. 1391-1394, May 1998.

Rinaldi, C. Aldo, A Randomized Prospective Study of Single Coil Versus Dual Coil Defibrillation in Patients With Ventricular Arrhythmias Undergoing Implantable Cardioverter Defibrillator Therapy, PACE, vol. 26, pp. 1684-1690, Aug. 2003.

Schwartzman, David, M.D., et al., Serial Defibrillation Lead Impedance in Patients with Epicardial and Nonthoracotomy Lead Systems, Journal of Cardiovascular Electrophysiology, vol. 7, No. 8, pp. 697-703, Aug. 1996.

Sandstedt, Bengt, et al., Bidirectioinal Defibrillation Using Implantable Defibrillators: A Prospective Randomized Comparison Between Pectoral and Abdominal Active Generators, PACE, vol. 24, Part I, pp. 1343-1353, Sep. 2001.

Schulte, B., et al., Dual-Coil vs. Single-Coil Active pectoral Implantable Defibrillator Lead Systems: Defibrillation Lead Requirements and Probability of Defibrillation Success at Multiples of the Defibrillation Energy Requirements, Europace, vol. 3, pp. 177-180, Jul. 2001.

U.S. Appl. No. 60/486,062 filed Jul. 10, 2003; Inventors: Hong et al.
U.S. Appl. No. 10/704,376 filed Nov. 7, 2003; Inventor: Lau.
U.S. Appl. No. 60/535,888 filed Jan. 12, 2004; Inventors: Fishler et al.

Bencini, Adriano, M.D., The "Pneumomassage" of the Heart, Surgery, vol. 39, No. 3, Mar. 1956.

Anstadt, George L., et al., A New Instrument for Prolonged Mechanical Cardiac Massage, Abstracts of the 38th Scientific Sessions, Supplement II to Circulation, vols. 31 and 32, pp. 375-384, Oct. 1965.

Paling, D.F., Warp Knitting Technology, 1970.

Edie, Richard N., M.D., et al., Surgical Repair of Single Ventricle, The Journal of Thoracic and Cardiovascular Surgery, vol. 66, No. 3, pp. 350-360, Sep. 1972.

McGoon, Dwight C., M.D., et al., Correction of the Univentricular Heart Having Two Atriovantricular Valves, The Journal of Thoracic and Cardiovascular Surgery, vol. 74, No. 2, pp. 218-226, Aug. 1977.

Doty, Donald B., et al., Septation of teh Univentricular Heart: Transatrial Approach, The Journal of Thoracic and Cardiovascular Surgery, vol. 78, No. 3, pp. 424-430, Sep. 1979.

Schetky, L. McDonald, Shap- Memory Alloys, Scientific American, vol. 241, No. 5, pp. 74-82, Nov. 1979.

Melton, K.N., et al., Alloys With Two-Shape Memory Effect, Mechanical Engineering, pp. 42-43, Mar. 1980.

Feldt, Robert H., M.D., et al., Current Status of the Septation Procedure for Univentricular Heart, The Journal of Thoracic and Cardiovascular Surgery, vol. 82, No. 1, pp. 93-97, Jul. 1981.

Carpenter, A., et al., Myocardial Substitution With Stimulated Skeletal Muscle: First Successful Clinical Case, The Lancet, Jun. 1, 1985.

Anstadt, Mark P. et al., Direct Mechanical Ventricular Actuation: A Review, Resuscitation, pp. 7-23, 1991.

Anstadt, Mark P., M.D., et al., Pulsatile Reperfusion After Cardiac Arrest Improves Neurologic Outcome, American Surgery, vol. 214, No. 4, pp. 478-490, Oct. 1991.

Schumacker, Harris B., Jr., Chapter 21: Cardiac Aneurysms, The Evolution of Cardiac Surgery, pp. 159-165, 1992.

Savage, Edward B., M.D., et al., Repair of Left Ventricular Aneurysm, The Journal of Thoracic and Cardiovascular Surgery, vol. 104, No. 3, pp. 752-762, Sep. 1992.

Carpentier, Alain, M.D., Ph.D., et al., Dynamic Cardiomyoplasty at Seven Years, The Journal of Thoracic and Cardiovascular Surgery, vol. 106, No. 1, pp. 42-54, Jul. 1993.

Capouya, Eli R., M.D., et al., Girdling Effect of Nonstimulated Cardiomyoplasty on Left Ventricular Function, Annals of Thoracic Surgeons, vol. 56, pp. 867-871, 1993.

Chekanov, Valeri, M.D., Ph.D., Nonstimulated Cardiomyoplasty Wrap Attenuated the Degree of Left Ventricular Enlargement, Annals of Thoracic Surgeons, vol. 57, pp. 1684-1690, 1997.

Chiu, Ray C.-J, Using Skeletal Muscle for Cardiac Assistance, Scientific American, pp. 68-77, Nov./Dec. 1994.

Kass, David A., M.D., et al., Reverse Remodeling From Cardiomyoplasty in Human Heart Failure: External Constraint Versus Active Assist, Circulation, vol. 91, No. 9, pp. 2314-2318, May 1, 1995.

Vaynblat, Mikhail, M.D., et al., Cardiac Binding in Experimental Heart Failure, Annals of Thoracic Surgery (Abstract), Supplement to Circulation, vol. 92, Suppl. 1, 1995.

Levin, Howard R., M.D., et al., Reversal of Chronic Ventricular Dilation in Patients With End-Stage Cardiomyopathy by Prolonged Mechanical Unloading. Circulation, vol. 91, No. 11, pp. 2717-2720, 1995.

Chaudhry, Pervaiz A., M.D., et al., Acute Ventricular Reduction with Acorn's Cardiac Support Device Prevents Progressive Left Ventricular Dysfunction and Remodeling in Dogs With Advanced Heart Failure, Cardiothoracic Surgery, pp. 146-148, 1996.

Oh, Joong Hwan, M.D., et al., Mechanisms of Dynamic Cardiomyoplasty: Current Concepts, Journal of Cardiac Surgery, vol. 11, pp. 194-199, 1996.

Wood, Alastair J.J., M.D., Editor, Review of Cohn, Jay N., M.D., The Management of Chronic Heart Failure, The New England Journal of Medicine: Review Article, vol. 335, No. 7, pp. 490-498, Aug. 15, 1996.

Badhwar, Vinay, Power Generation From Four Skeletal Muscle Configurations Design Implications for a Muscle Powered Cardiac Assist Device, ASAIO Journal, vol. 43, pp. M651-M657, 1997.

Vaynblat, Mikhail, M.D., et al., Cardiac Binding in Experimental Heart Failure, Annals of Thoracic Surgery, vol. 64, pp. 81-85, 1997.

Westaby, Stephen, et al., Landmarks in Cardiac Surgery, pp. 198-199, 1997.

Cox, James L., Left Ventricular Aneurysms: Pathophysiologic Observations and Standard Resection, Seminars in Thoracic and Cardiovascular Surgery, vol. 9, No. 2, pp. 113-122, Apr. 1997.

Coletta, C., et al., Prognostic Value of Left Ventricular Volume Response During Dobutamine Stress Echocardiography, European Heart Journal, vol. 18, pp. 1599-1603, Oct. 1997.

Capomolla, Soccorso, M.D., et al., Dobutamine and Nitroprusside Infusion in Patients With Severe Congestive Heart Failure: Hemodynamic Improvement by Discordant Effects on Mitral Regurgitation, Left Atrial Function, and Ventricular Function, American Heart Journal, 1089-1098, Dec. 1997.

Oh, Joong Hwan, The Effects of Prosthetic Cardiac Binding and Adynamic Cardiomyoplasty in a Model of Dilated Cardiomyopathy, The Journal of Thoracic and Cardiovascular Surgery, vol. 116, No. 1, pp. 148-153, 1998.

Cohn, Jay N., M.D., Preventing Congestive Heart Failure, American Family Physician, 6 pages, Apr. 15, 1998.

Cohn, Jay N., M.D., Structural Basis for Heart Failure: Ventricular Remodeling and Its Pharmacological Inhibition, Circulation, vol. 91, No. 10, pp. 2504-2507, May 15, 1995.

Gaudron, Peter, M.D., et al., Progressive Left Ventricular Dysfunction and Remodeling After Myocardial Infarction, Circulation, vol. 87, pp. 755-763, Mar. 1993.

Pfeiffer, Marc A., M.D., et al., Ventricular Remodeling After Myocardial Infarction: Experimental Observations and Clinical Implications, Circulation, vol. 81, No. 4, pp. 1161-1172, Apr. 1990.

Guasp, Francisco Torrent, Una protesis contentiva para el tratamiento de le microcardiopatia dilatads, *Revista Española de Cardiologia*, vol. 51, No. 7, Jul. 1998.

Power, J.M., et al., Passive Ventricular Constraint Amends the Course of Heart Failure: A Study in an Ovine Model of Dilated Cardiomyopathy, *Cardiovascular Research*, vol. 44, pp. 549-555, 1999.

Frazier, O.H., M.D., et al., Left Ventricular Assist System as a Bridge to Myocardial Recovery, *Annals of Thoracic Surgery*, vol. 68, pp. 734-741, 1999.

Melvin, David B., Ventricular Radium Reduction Without Resection: A Computational Analysis, *ASAIO Journal*, pp. 160-165, 1999.

*Abstracts—Heart Failure*, JACC Feb. 1999.

Raman, Jai S., FRACS, et al., Ventricular Containment as an Adjunctive Procedure in Ischemic Cardiomyopathy: Early Results, *Annals of Thoracic Surgery*, vol. 70, pp. 1124-1126, Jan. 2000.

McCarthy, Patrick M., et al., Device Based Left Ventricular Shape Change Immediately Reduces Left Ventricular Volume and Increases Ejection Fraction in a Pacing Induced Cardiomyopathy Model in Dogs, JACC, Feb. 2000.

Chaudhry, Pervaiz A., M.D., et al., Passive Epicardial Containment Prevents Ventricular Remodeling in Heart Failure, *Annals of Thoracic Surgeons*, vol. 70, pp. 1275-1280, 2000.

Acorn Cardiovascular, Inc., *CSD Specifications Acorn Cardiac Support Device*, 2000.

Heart "jacket" could help stop heart failure progression, *Clinicia*, No. 916, Jul. 2000.

Acorn Cardiovascular, Inc., *CorCap™ Cardiac Support Device* Pamphlet, Jun. 2001.

Medtronic's InSync Cardiac Resynchronization Therapy Device Approved by FDA, (Press Release) Aug. 28, 2001.

Acorn Cardiovascular, Inc., Acorn Highlights: ESC, Schedule, Sep. 2001.

Oz, Mehmet C., M.D., Passive Ventricular Constraint for the Treatment of Congestive Heart Failure, *Annals of Thoracic Surgery*, vol. 71, pp. 5185-5187, 2001.

Abstract Supplement, *European Heart Journal*, vol. 22, Sep. 2001.

Gorman, J., Self-Sutures: New Material Knots Up On Its Own, *Science News*, vol. 161, p. 262, Apr. 27, 2002.

Mann, Douglas L., M.D., Basic Mechanisms of Remodeling and Reverse Remodeling, presented at 6th Annual Scientific Meeting of the Heart Failure Society of America, Sep. 24, 2002.

Bocchi, Edimar a., M.D., Arrhythmias and Sudden Death After Dynamic Cardiomyoplasty, *Circulation*, vol. 90, No. 5, Part 2, pp. 11-107 thru 11-111, Nov. 1994.

Chachques, Juan C., M.D., Study of Muscular and Ventricular Function in Dynamic Cardiomyoplasty: A Ten-Year Follow-Up, *The Journal of Heart and Lung Transplantation*, vol. 16, No. 8, pp. 854-868, Aug. 1997.

Dullum, Mercedes K.C., M.D., et al., Less Invasive Surgical Management of Heart Failure by Cardiac Support Device Implantation on the Beating Heart, The Heart Surgery Forum, #2001-1818, pp. 361-363, Jan. 4-7, 2001.

Macris, Michael P. M.D., et al., Minimally Invasive Access of the Normal Preicardium: Initial Clinical Experience with a Novel Device, *Clinical Cardiology*, vol. 22 (Suppl. I), pp. 1-36 thru 1-39, 1999.

Thakur, Ranjan K., M.D., et al., Latissimus Dorsi Dynamic Cardiomyoplasty: Role of Combined ICD Implantation, *Journal of Cardiac Surgery*, vol. 10, pp. 295-297, 1995.

U.S. Appl. No. 09/634,043, filed Aug. 8, 2000.
U.S. Appl. No. 09/952,145, filed Sep. 10, 2001.
U.S. Appl. No. 10/242,016, filed Sep. 10, 2002.
U.S. Appl. No. 10/287,723, filed Oct. 31, 2002.
U.S. Appl. No. 10/314,696, filed Dec. 9, 2002.
U.S. Appl. No. 10/287,723, filed Jan. 4, 2004.
U.S. Appl. No. 60/458,991, filed Mar. 28, 2003.
U.S. Appl. No. 60/486,062, filed Jul. 10, 2003.
U.S. Appl. No. 10/693,577, filed Oct. 23, 2003.
U.S. Appl. No. 10/694,646, filed Oct. 27, 2003.
U.S. Appl. No. 10/698,237, filed Oct. 31, 2003.
U.S. Appl. No. 10/704,376, filed Nov. 7, 2003.
U.S. Appl. No. 10/705,989, filed Nov. 12, 2003.
U.S. Appl. No. 10/714,189, filed Nov. 13, 2003.
U.S. Appl. No. 10/715,150, filed Nov. 17, 2003.
U.S. Appl. No. 10/754,174, filed Jan. 9, 2004.
U.S. Appl. No. 10/754,264, filed Jan. 9, 2004.
U.S. Appl. No. 10/754,852, filed Jan. 9, 2004.
U.S. Appl. No. 60/535,888, filed Jan. 12, 2004.
U.S. Appl. No. 10/777,451, filed Feb. 12, 2004.
U.S. Appl. No. 10/788,791, filed Feb. 27, 2004.
U.S. Appl. No. 10/704,376, filed Mar. 3, 2004.
U.S. Appl. No. 10/705,574, filed Mar. 5, 2004.

Chiu, Ray C.-J, Using Skeletal Muscle for Cardiac Assistance, *Scientific American*, Nov./Dec. 1994.

David A. Kass, M.D., et al., Reverse Remodeling From Cardiomyoplasty in Human Heart Failure, *Circulation*, vol. 91, No. 9, May 1, 1995.

Howard R. Levin, M.D., et al., Reversal of Chronic Ventricular Dilation in Patients With End-Stage Cardiomyopathy by Prolonged Mechanical Unloading, *Circulation*, vol. 91, No. 11, Jun. 1995.

Eli R. Capouya, M.D., et al, Girdling Effect on Nonstimulated Cardiomyoplasty on Left Ventricular Function, *Society of Thoracic Surgeons*, pp. 867-871, 1993.

\* cited by examiner

HEART FAILURE TREATMENT DEVICE AND METHOD

RELATED APPLICATIONS

This application claims priority to U.S. Provisional Application No. 60/335,437, which was filed on Oct. 31, 2001, the entirety of which is hereby incorporated by reference.

BACKGROUND OF THE INVENTION

1. Field of the Invention

The present invention relates to a device for treating heart failure. More specifically, the invention relates to a cardiac harness configured to be fit around at least a portion of a patient's heart.

2. Description of the Related Art

Congestive heart failure ("CHF") is characterized by the failure of the heart to pump blood at sufficient flow rates to meet the metabolic demand of tissues, especially the demand for oxygen. One characteristic of CHF is remodeling of at least portions of a patient's heart. Remodeling involves physical changes to the size, shape and thickness of the heart wall. For example, a damaged left ventricle may have some localized thinning and stretching of a portion of the myocardium. The thinned portion of the myocardium often is functionally impaired, and other portions of the myocardium attempt to compensate. As a result, the other portions of the myocardium may expand so that the stroke volume of the ventricle is maintained notwithstanding the impaired zone of the myocardium. Such expansion may cause the left ventricle to assume a somewhat spherical shape.

Cardiac remodeling often subjects the heart wall to increased wall tension or stress, which further impairs the heart's functional performance. Often, the heart wall will dilate further in order to compensate for the impairment caused by such increased stress. Thus, a vicious cycle can result, in which dilation leads to further dilation and greater functional impairment.

Historically, congestive heart failure has been managed with a variety of drugs. Devices have also been used to improve cardiac output. For example, left ventricular assist pumps help the heart to pump blood. Multi-chamber pacing has also been employed to optimally synchronize the beating of the heart chambers to improve cardiac output. Various skeletal muscles, such as the latissimus dorsi, have been used to assist ventricular pumping. Researchers and cardiac surgeons have also experimented with prosthetic "girdles" disposed around the heart. One such design is a prosthetic "sock" or "jacket" that is wrapped around the heart.

Although some of the above-discussed devices hold promise, there remains a need in the art for a device for treating CHF to prevent a remodeled heart from further remodeling and/or help reverse remodeling of a diseased heart.

SUMMARY OF THE INVENTION

In accordance with one aspect of the present invention, an organ reshaping device is provided. A reshaping member of the device is comprised of elastic material, and is configured to be placed about at least a portion of the organ such that the elastic material is subject to substantially the same environmental conditions as the surface of the organ. The elastic material has an elastic characteristic which: a) changes upon alteration of the environmental conditions beyond a threshold level; and b) remains at least partially changed upon return of the environmental conditions from beyond the threshold level to an unaltered level.

In accordance with another embodiment, an organ reshaping device for exerting a force on an organ comprises a bending member configured to be placed in contact with the organ so that the organ urges the bending member into a deformed shape relative to an at rest shape of the member, and the bending member exerts a bending force on the organ. The bending member has a first elastic deflection range and a second elastic deflection range, and may operate over only one deflection range at a time. Further, the bending member is responsive to inputs to shift between the first and second elastic deflection ranges.

In accordance with still another aspect of the invention, a method is provided comprising providing a harness comprised of a shape memory material and placing the harness around an organ while the shape memory material is in a generally martensitic state. The method further includes raising the temperature of the shape memory material to transform the shape memory material to a generally austenitic state so that the harness generally hugs the surface of the organ.

In accordance with a further aspect, a method of reshaping an organ from an initial shape to a desired shape is provided. A reshaping harness is placed about at least a portion of the organ, said placing comprising elastically deforming the harness such that reshaping forces in response to the deformation are applied by the harness to the organ within an elastic deflection range of the harness. The reshaping forces urge the organ from the initial shape towards an intermediate shape between the initial shape and the desired shape. After the organ has assumed the intermediate shape, the elastic deflection range of the harness is altered so that the reshaping forces act within the altered deflection range to urge the organ from the intermediate shape towards the desired shape.

In accordance with yet another aspect, the present invention provides an organ shaping device for exerting a force on an organ. A bending member is configured to be placed around at least a portion of the organ so that the organ urges the bending member into an expanded deformed shape relative to an at rest shape of the member, and the bending member exerts a bending force on the organ that tends to squeeze the organ. The bending member comprises a material configured to increase in stiffness as the temperature of the material is increased within an operational range of temperatures.

In accordance with a further aspect, the material comprises a shape memory material.

In accordance with another aspect of the present invention, a method comprises providing a harness comprised of a shape memory material having an at rest shape and placing the harness around an organ. The placing comprises expandingly deforming the harness from the at rest shape so that the harness fits around at least a portion of the organ and the harness applies a pressure onto the organ in resistance to the deformation. The shape memory material is in a generally austenitic state when at a temperature of the organ.

Further features and advantages of the present invention will become apparent to one of skill in the art in view of the Detailed Description of Preferred Embodiments which follows, when considered together with the attached drawings and claims.

DETAILED DESCRIPTION OF PREFERRED EMBODIMENTS

As discussed in Applicants' co-pending application entitled "Expandable Cardiac Harness For Treating Congestive Heart Failure," Ser. No. 09/634,043, which was filed on Aug. 8, 2000, the entirety of which is hereby expressly incorporated by reference, it is anticipated that remodeling of a diseased heart can be resisted or even reversed by alleviating the wall stresses in such a heart. The present application discusses certain embodiments, methods of manufacture, methods of use, and advantages of devices for reducing such cardiac wall stresses. Additional embodiments and aspects are also discussed in Applicants' co-pending application entitled "Device for Treating Heart Failure," Ser. No. 10/242,016, which was filed on Sep. 10, 2002, the entirety of which is hereby expressly incorporated by reference.

Figure 1:
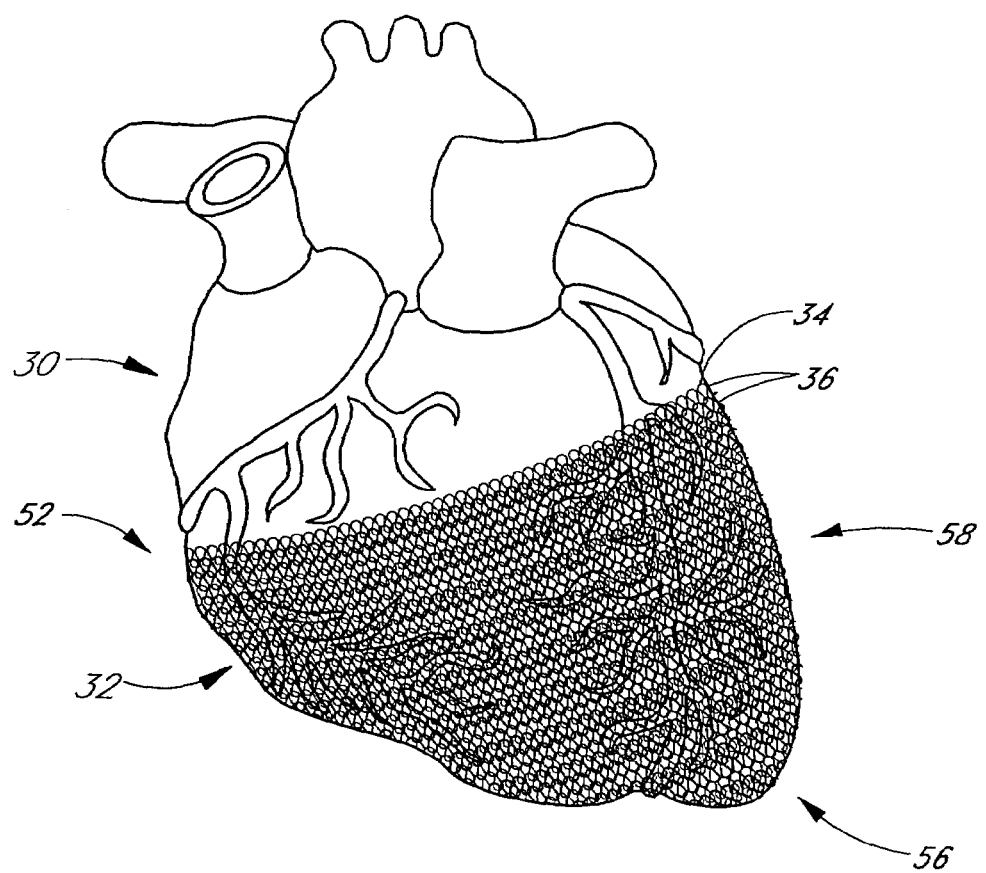
FIG. 1 is a schematic view of a heart with cardiac harness placed thereon.

FIG. 1 illustrates a mammalian heart 30 having a cardiac wall stress reduction device in the form of a harness 32 applied to it. The cardiac harness 32 comprises a series of hinges or spring elements 34 that circumscribe the heart 30 and, collectively, apply a mild compressive force on the heart so as to alleviate wall stresses.

The term "cardiac harness" as used herein is a broad term that refers to a device fit onto a patient's heart to apply a compressive force on the heart during at least a portion of the cardiac cycle. Other devices that are intended to be fit onto a heart and are referred to in the art as "girdles," "socks," "jackets," or the like are included within the meaning of "cardiac harness."

Figure 2A:
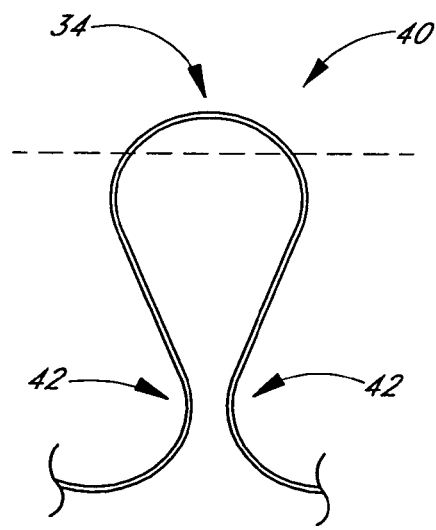
FIG. 2A-2B illustrate a spring hinge in a relaxed position and under tension.
Figure 2B:
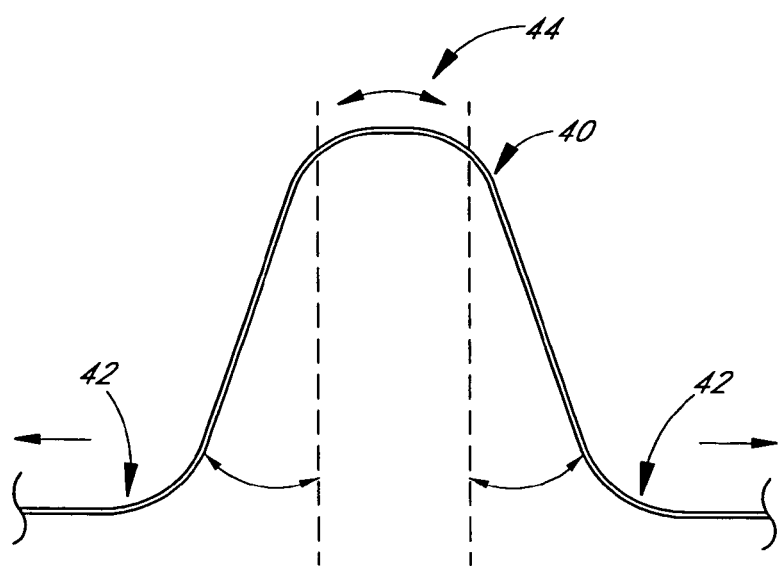

The cardiac harness 32 illustrated in FIG. 1 comprises at least one undulating strand 36 comprising a series of spring elements 34 referred to as hinges or spring hinges that are configured to deform as the heart 30 expands during filling. Each hinge 34 provides substantially unidirectional elasticity, in that it acts in one direction and does not provide much elasticity in the direction perpendicular to that direction. For example, FIG. 2A shows one embodiment of a hinge member 34 at rest. The hinge member 34 has a central portion 40 and a pair of arms 42. As the arms are pulled, as shown in FIG. 2B, a bending moment 44 is imposed on the central portion 40. The bending moment 44 urges the hinge member 34 back to its relaxed condition. Note that a typical strand comprises a series of such hinges, and that the hinges 34 are adapted to elastically expand and retract in the direction of the strand 36.

In the embodiment illustrated in FIG. 1, the strands 36 of spring elements 34 are constructed of extruded wire that is deformed to form the spring elements. Although FIG. 1 shows adjacent strands 36 interwoven one with another, it is to be understood that, in additional embodiments, adjacent strands 36 may not overlay or touch one another.

Figure 3:
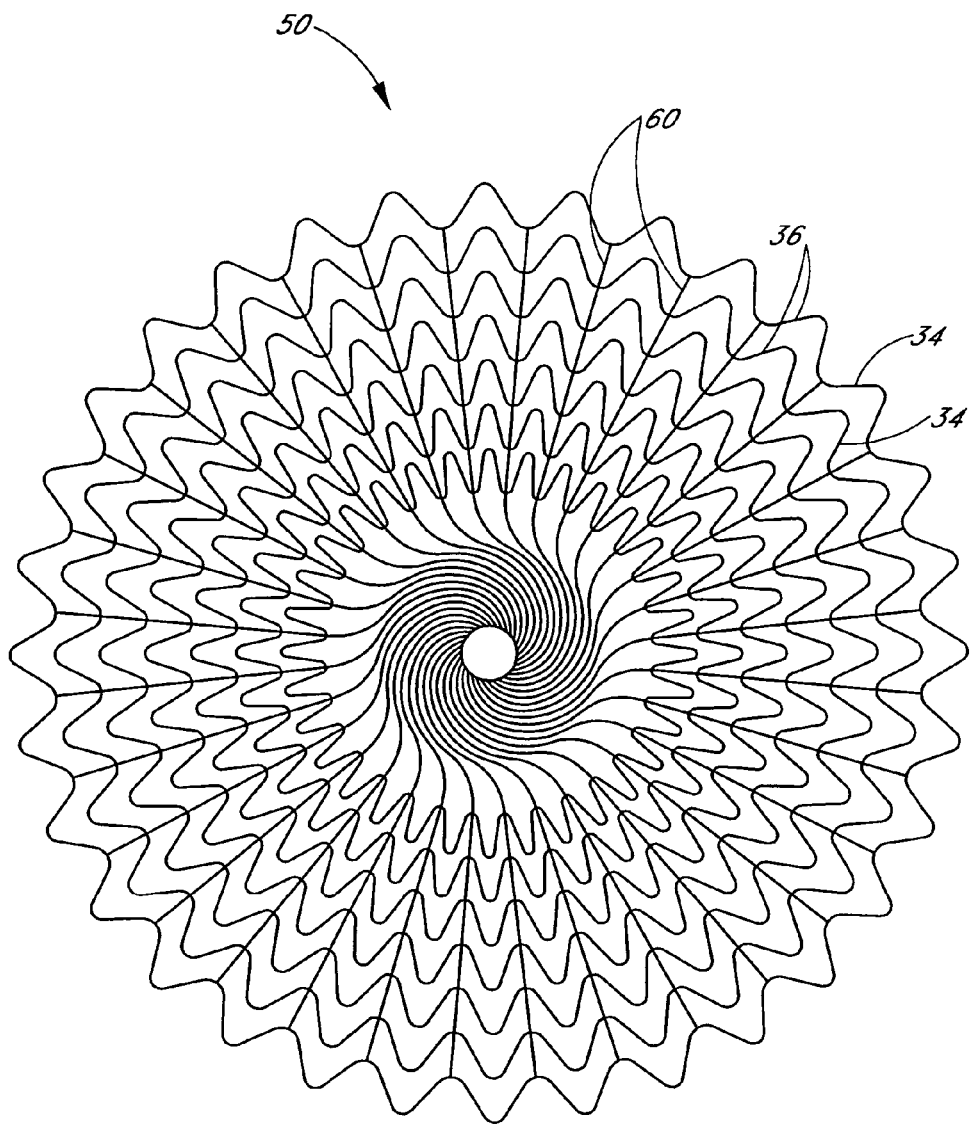
FIG. 3 shows an embodiment of a cardiac harness that has been cut out of a flat sheet of material.
Figure 4:
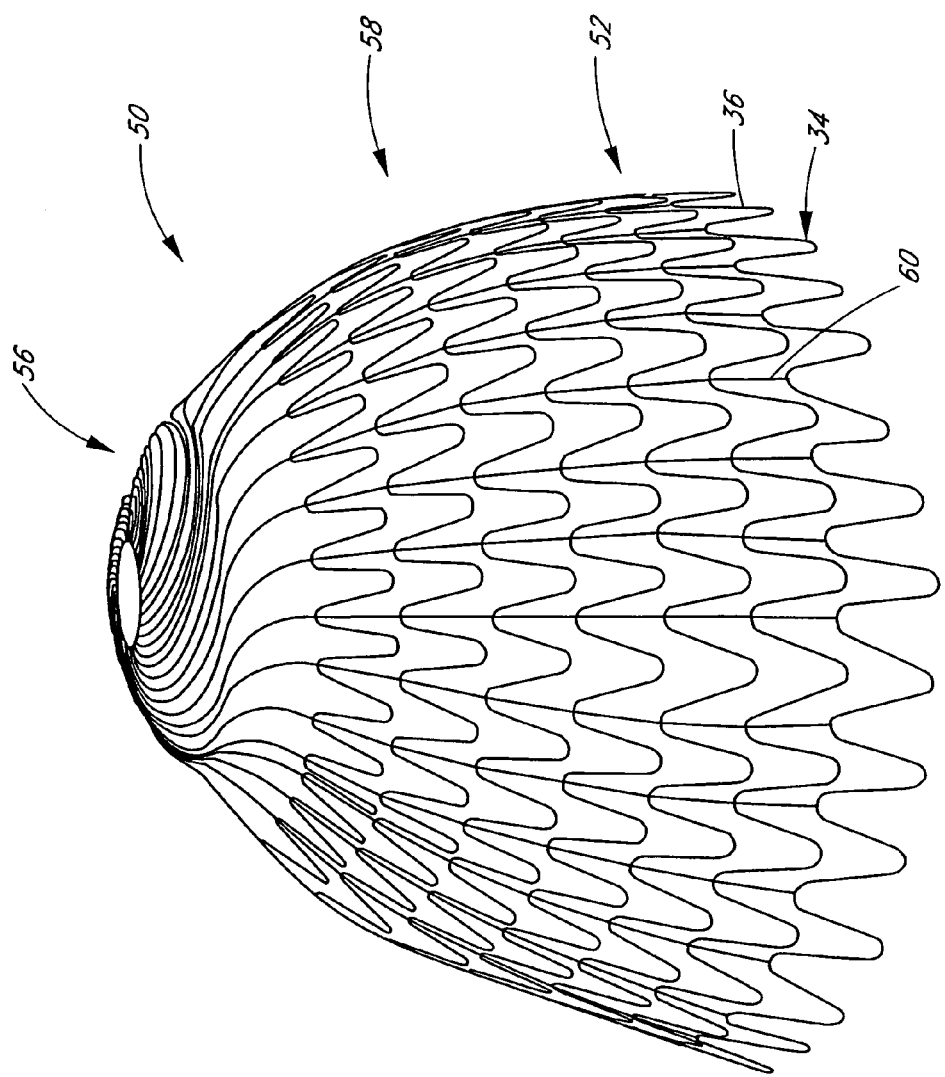
FIG. 4 shows the cardiac harness of FIG. 3 formed into a shape configured to fit about a heart.

FIGS. 3 and 4 illustrate another preferred embodiment of a cardiac harness 50, shown at two points during manufacture of such a harness. In the illustrated embodiment, the harness 50 is first formed from a relatively thin, flat sheet of material. Any method can be used to form the harness. For example, in one embodiment, the harness is photochemically etched from the material; in another embodiment, the harness is laser-cut from the thin sheet of material. The embodiment shown in FIGS. 3 and 4 has been etched from a thin sheet of Nitinol, which is a superelastic material that also exhibits shape memory properties. The flat sheet of material is draped over a form, die or the like, and is formed to generally take on the shape of at least a portion of a heart.

With reference to FIGS. 1 and 4, the illustrated embodiments of the cardiac harnesses 32, 50 comprise a base portion 52, which is sized and configured to generally engage and fit onto a base region of a patient's heart; an apex portion 56, which is sized and shaped so as to generally engage and fit on an apex region of a patient's heart; and a medial portion 58 between the base and apex portions.

In the embodiment shown in FIGS. 3 and 4, the harness 50 comprises strands or rows 36 of undulating wire. As discussed above, the undulations comprise hinges/spring elements 34 which are elastically bendable in a desired direction. Some of the strands 36 are connected to each other by interconnecting elements 60. The interconnecting elements 60 help maintain the position of the strands 36 relative to one another. Preferably the interconnecting elements 60 allow some relative movement between adjacent strands 36.

As discussed above, the undulating spring elements 34 exert a force in resistance to expansion of the heart 30. Collectively, the force exerted by the spring elements tends toward compressing the heart, thus alleviating wall stresses in the heart as the heart expands. Accordingly, the harness helps to decrease the workload of the heart, enabling the heart to more effectively pump blood through the patient's body and enabling the heart an opportunity to heal itself. It should be understood that several arrangements and configurations of spring members can be used to create a mildly compressive force on the heart so as to reduce wall stresses. For example, spring members can be disposed over only a portion of the circumference of the heart or harness.

Figure 5A:
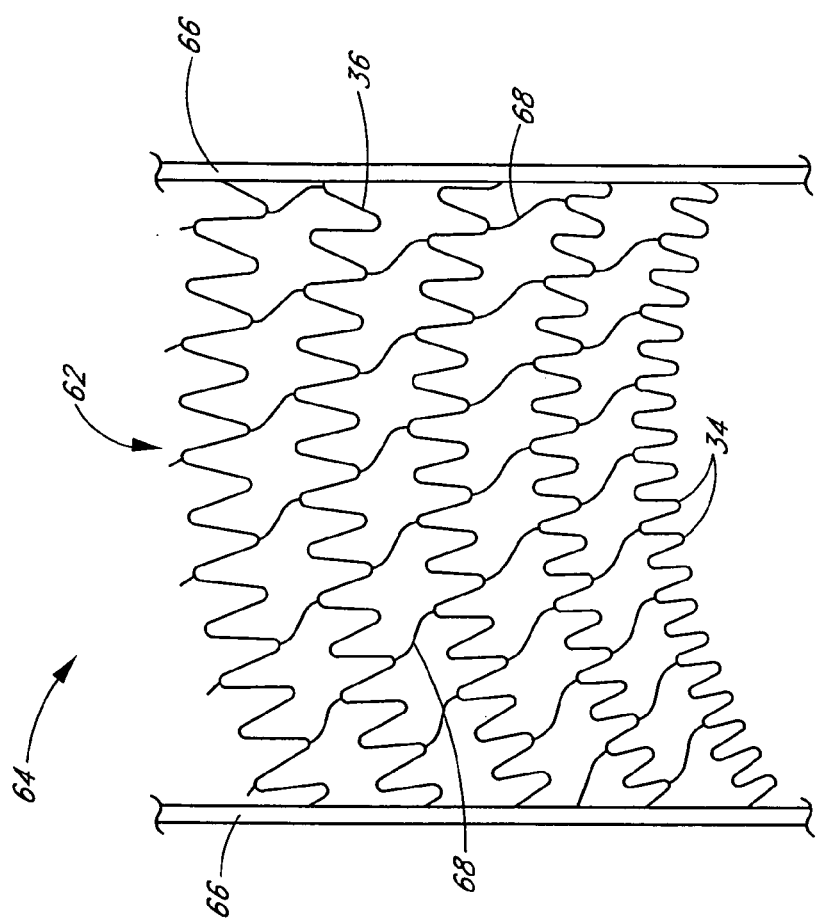
FIG. 5A shows a portion of an embodiment of a cardiac harness disposed on a testing apparatus in a relaxed position.
Figure 5B:
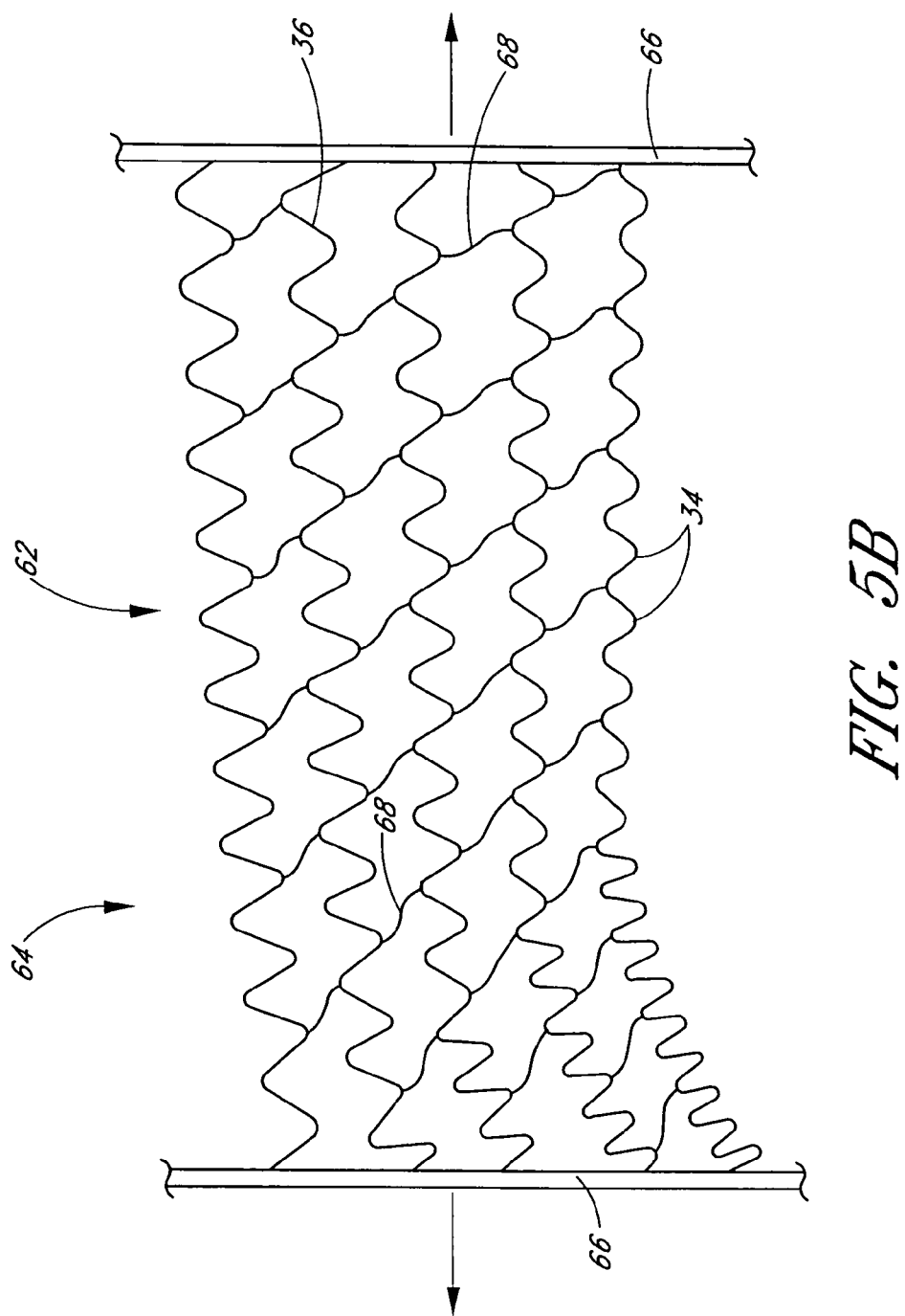
FIG. 5B shows the portion of FIG. 5A in a stretched position.

As can be appreciated, a variety of hinge/spring designs and arrangements can be used in embodiments of cardiac harnesses. FIGS. 5A and B show a portion 62 of another embodiment of a cardiac harness 64 disposed in a testing apparatus 66. The portion 62 is shown in a relaxed position (FIG. 5A) and in a deformed, stretched position (FIG. 5B). In this embodiment, the cardiac harness 64 comprises a plurality of rows 36 of undulating spring elements 34 that are connected one to another with angled interconnecting elements 68. Preferably, the interconnecting elements 68 are also capable of deflecting in a manner so as to act as springs. As can be seen in the figures, when an outside stress from the testing apparatus 66 deforms the harness 64, both the undulating rows 36 of springs 34 and the interconnecting elements 68 deform. In this manner, the undulating rows 36 of springs can move relative to one another even though they are still connected via the interconnecting elements 68. However, the interconnecting elements 68 distribute stresses between the rows 36.

Figure 6A:
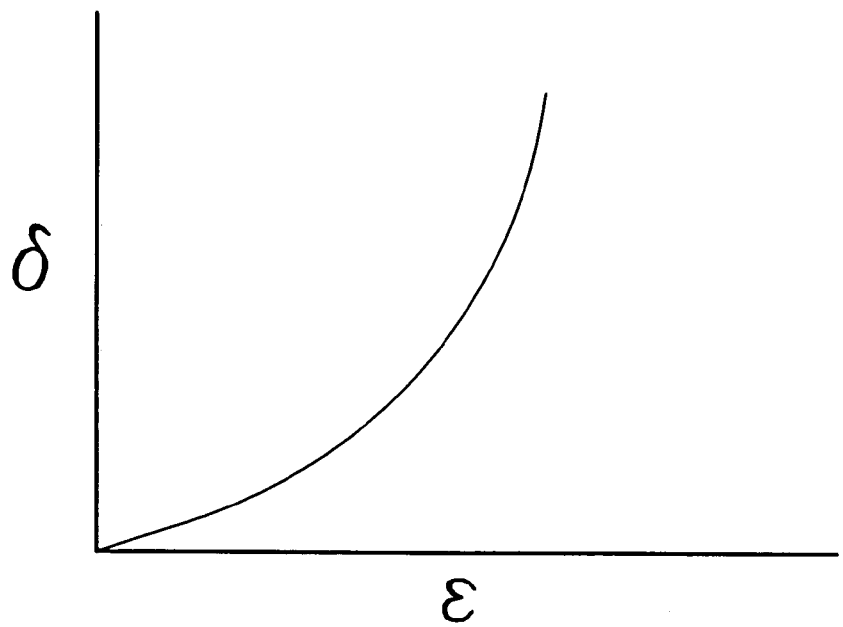
FIG. 6A illustrates a stress/strain curve of a typical undulating spring.
Figure 6B:
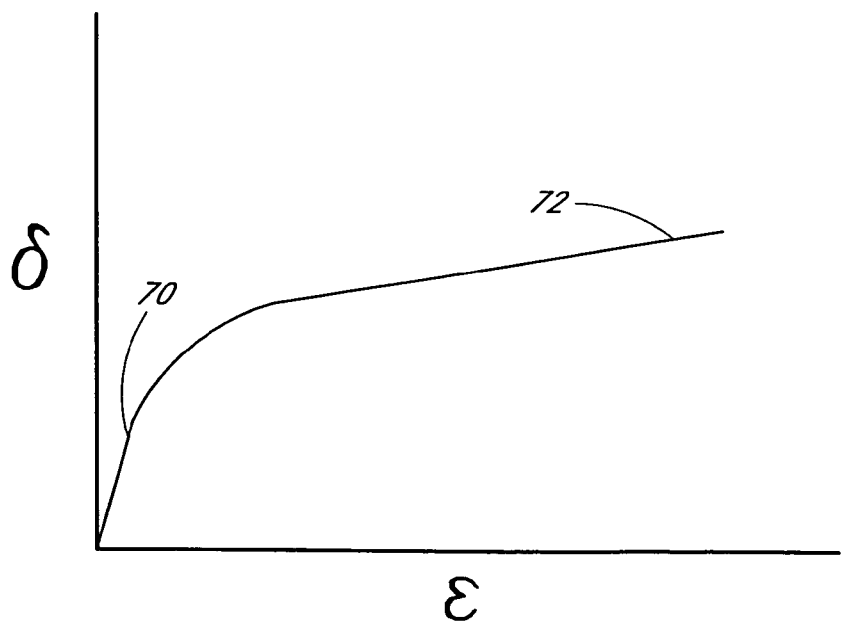
FIG. 6B illustrates a stress/strain curve of the cardiac harness embodiment depicted in FIGS. 5A and B.

The embodiment shown in FIGS. 5A and B also exhibits advantageous overall deformation qualities. With next reference to FIG. 6A, a stress/strain curve 69 of a typical undulating spring is shown. As can be seen, as deformation (strain) increases, the corresponding stress also increases. The embodiment of FIGS. 5A and B, however, has been shown to exhibit stress/strain qualities more similar to that as shown in FIG. 6B. As illustrated, after application of an initial stress load 70 to begin deformation, further deformation of the harness is achieved on a generally flat or low-slope stress plateau 72. The stress load corresponds to a force or pressure that will be exerted by the harness on the heart. In operation, when initial deformation of the harness is complete, such as when it is fit about a patient's heart, the harness will operate in an elastic deformation range with a maximum stress value that is found on the stress plateau portion of the stress/strain curve. This is helpful for improving the safety of the device because the harness is designed so that the stress plateau 72 never exceeds certain stress levels during its working range of deformation. Accordingly, a harness having this configuration is designed so as to never exert a pressure on the heart that is greater than a predetermined "safe" pressure level. For example, in one embodiment, a harness is configured so that the plateau stress associated with deformation over the working range of the device corresponds to a compressive force exerted by the device, which compressive force never exceeds a predetermined upper limit that may cause constriction of the heart.

Figure 7:
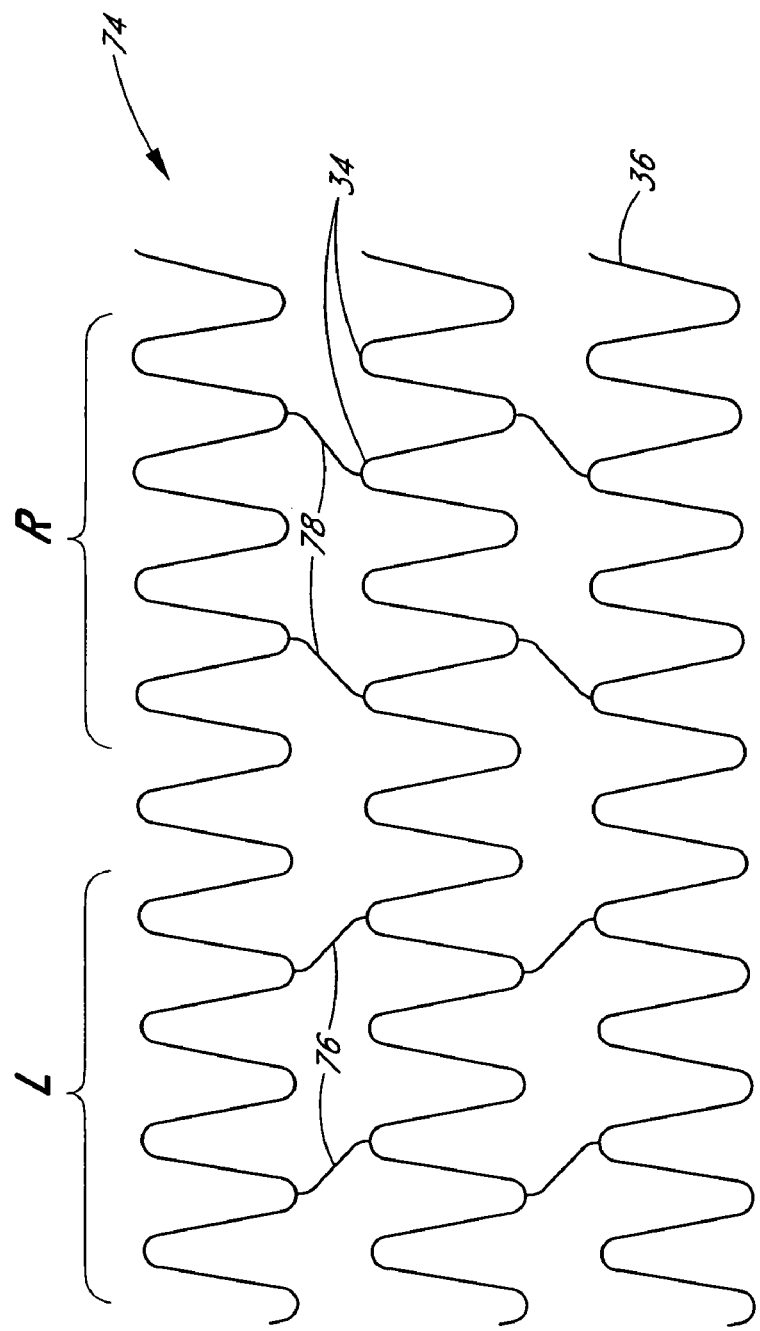
FIG. 7 shows a portion of another embodiment of a cardiac harness.

With next reference to FIG. 7, another embodiment of a cardiac harness 74 is illustrated wherein a right portion R of the harness is customized for the right side of the heart while a left portion L is customized for the left side of the heart. Heart muscle fibers are known to contract and expand generally unidirectionally. Muscle fibers on the right side of the heart follow a generally helical directional orientation in a first direction, while fibers on the left side of the heart follow a general helical directional orientation in a second direction. In the embodiment illustrated in FIG. 7, undulating rows 36 are connected by interconnecting elements 76, 78, but the interconnecting elements 76, 78, are specially arranged to better cooperate with the directional expansion and contraction of the muscle fibers in the left and right sides of the heart. More specifically, the interconnecting elements are arranged so as to be generally oblique to the direction of muscle fiber expansion and contraction, and more preferably to be substantially perpendicular to the direction of expansion and contraction. Thus, in the illustrated embodiment, the interconnecting elements 76 on the left side L of the harness 74 extend in generally different directions than the interconnecting elements 78 on the right side R of the harness 74. In this manner, the unidirectionally-contracting muscle fibers can take advantage of the spring characteristics of both the undulating rows 36 of springs 34 and the interconnecting elements 76, 78.

Figure 8:
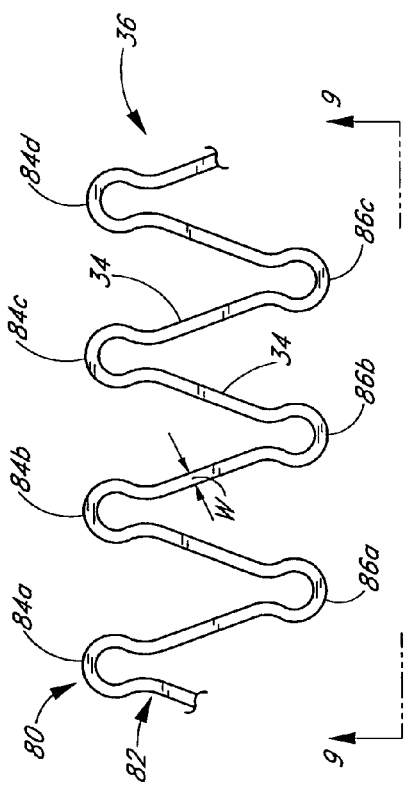
FIG. 8 shows a portion of another embodiment of a cardiac harness.
Figure 9:
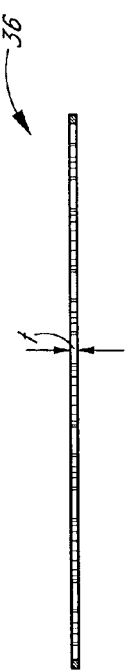
FIG. 9 shows the portion of FIG. 8 as viewed along line 9-9.
Figure 10:
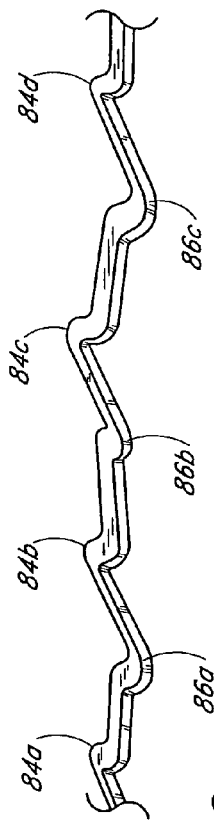
FIG. 10 shows the portion of FIG. 9 when pulled in tension.

With reference next to FIGS. 8-10, a portion 80 of an additional embodiment of a cardiac harness 82 is illustrated. More specifically, FIGS. 8-10 show a portion of a strand 36 of spring elements 34. In this embodiment, the spring elements 34 are configured in a "keyhole" configuration. As shown in FIGS. 8 and 9, a width w of the spring elements is greater than a thickness t thereof. Thus, an aspect ratio of the width w divided by the thickness t of the spring elements 34 is greater than one. As shown in FIG. 9, when the strand 36 is in a relaxed state, the spring elements 34 generally lie in a plane. With reference to FIG. 10, when the strand 36 is stretched longitudinally, the spring elements 34 exhibit out-of-plane deformation. Portions of the spring elements jut inwardly toward the heart epicardium. In the illustrated embodiment, successive peaks 84a-d and valleys 86a-c of adjacent spring elements 34 jut in generally opposite directions.

In accordance with further embodiments, one, several or all strands of a cardiac harness can have an aspect ratio configured such that out-of-plane deformation occurs during extension of the strand. In such embodiments, the inwardly-jutting portions are directed against the heart wall, increasing the friction between the harness and the heart. As such, the out-of-plane deformation helps anchor the harness to the heart. In a preferred embodiment, at least one strand of spring elements at or adjacent the base of the harness is configured so that the spring elements display out-of-plane deformation when the strand is longitudinally deformed. As such, anchoring forces are focused at or near the base of the harness. In further embodiments, one or several spring elements of a strand are configured to display such out-of-plane deformation.

In the embodiment illustrated in FIGS. 8-10, the aspect ratio is between about 1.8-2.0. It is to be understood, however, that other ranges of aspect ratios can be selected in order to obtain a magnitude of out-of-plane deformation desirable to help anchor the harness to the heart. The embodiment illustrated in FIGS. 8-10 has a generally rectangular cross-sectional shape. It is to be further understood that spring elements having other cross-sectional shapes, such as oval, can also display out-of-plane deformation.

During the cardiac cycle, cardiac wall stress is greatest at or near the end of diastole $D_F$, when the left ventricle has been filled with blood to be pumped into the vasculature of the patient. Conversely, wall stress is lowest at the beginning of diastole $D_S$, before the ventricle has been filled. In accordance with embodiments described in more detail below, a cardiac harness can be configured to take advantage of the properties of various materials in order to minimize the applied force at the beginning of diastole $D_S$ and maximize the applied force of the harness at or near the end of diastole $D_F$.

Figure 11:
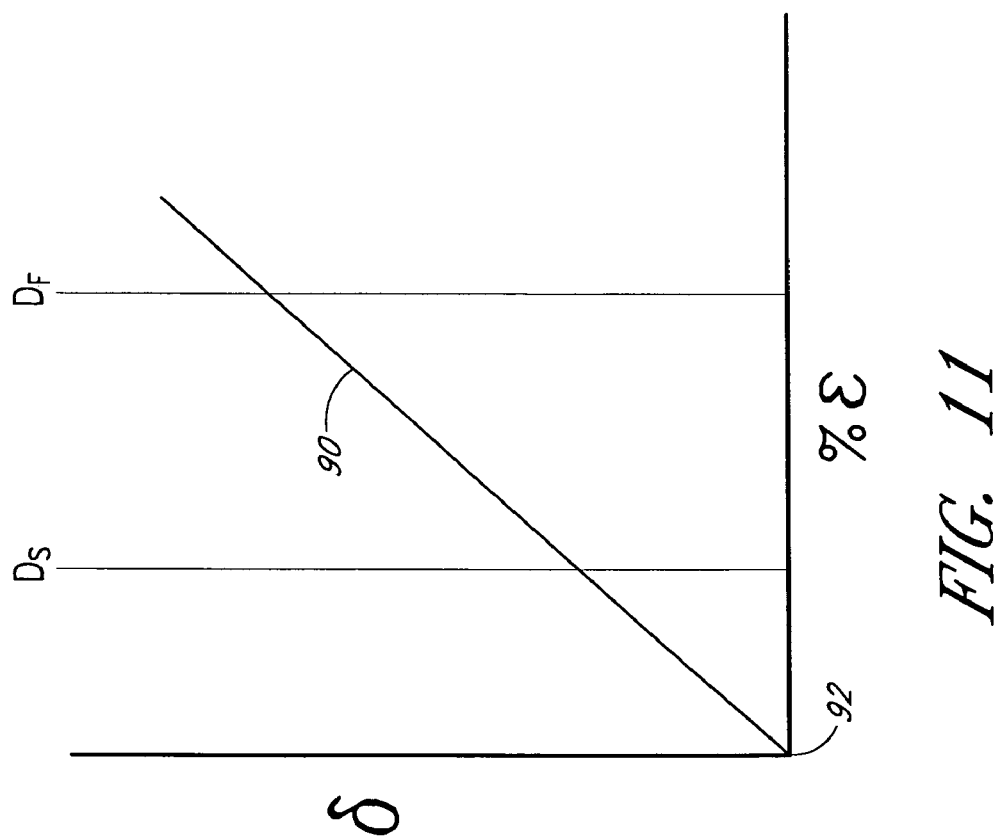
FIG. 11 illustrates a stress/strain curve generally representative of a typical stainless steel material.

With reference next to FIG. 11, a stress/strain curve 90 generally representative of a typical construction material, such as stainless steel, is provided. The illustrated curve shows the strain $\epsilon$ associated with particular applied stresses $\sigma$ in the material's range of elastic deformation. As can be seen, application of a specific stress $\sigma$ deforms the material, resulting in a characteristic percentage strain ϵ of the material. When the stress σ is released, the material returns to its at-rest condition 92.

The stress/strain characteristics of the material as illustrated in FIG. 11 hold true when the material is used to construct a cardiac harness such as a harness having structure similar to one or more of the embodiments discussed above. As discussed above, such a harness is specially configured to be placed on a beating heart. Of course, the size of the heart varies between the beginning of diastole $D_S$ and the end of diastole $D_F$. In the illustrated embodiment, the labels $D_S$ and $D_F$ have been applied to the stress/strain curve 90 to identify the stress and strain conditions of the harness material associated with the size of the heart (and harness) at the start and finish of diastole $D_S$, $D_F$, respectively. Since the harness expands and contracts with the beating heart, the harness can be expected to operate within a deflection range that includes $D_S$ and $D_F$.

As depicted in FIG. 11, the level of strain ϵ is greater at the end of diastole $D_F$ than at the beginning of diastole $D_S$. As would be expected, the level of stress σ at the end of diastole $D_F$ is also greater than at the beginning of diastole $D_S$. As such, the stainless steel harness exerts a greater compression force at the end of diastole $D_F$ than at the beginning of diastole $D_S$. In this manner, the greatest wall stresses are alleviated by the greatest compressive force of the cardiac harness, while lesser wall stresses are relieved by a significantly lesser compressive force.

Although the embodiment depicted in FIG. 11 has been described in connection with a stainless steel harness, it is to be understood that a somewhat similar stress/strain diagram can be expected for a variety of materials, such as, for example, other metals, polymeric materials, and composites. As such, a wide variety of materials can be used to achieve the above-described benefits for a diseased heart.

Figure 12:
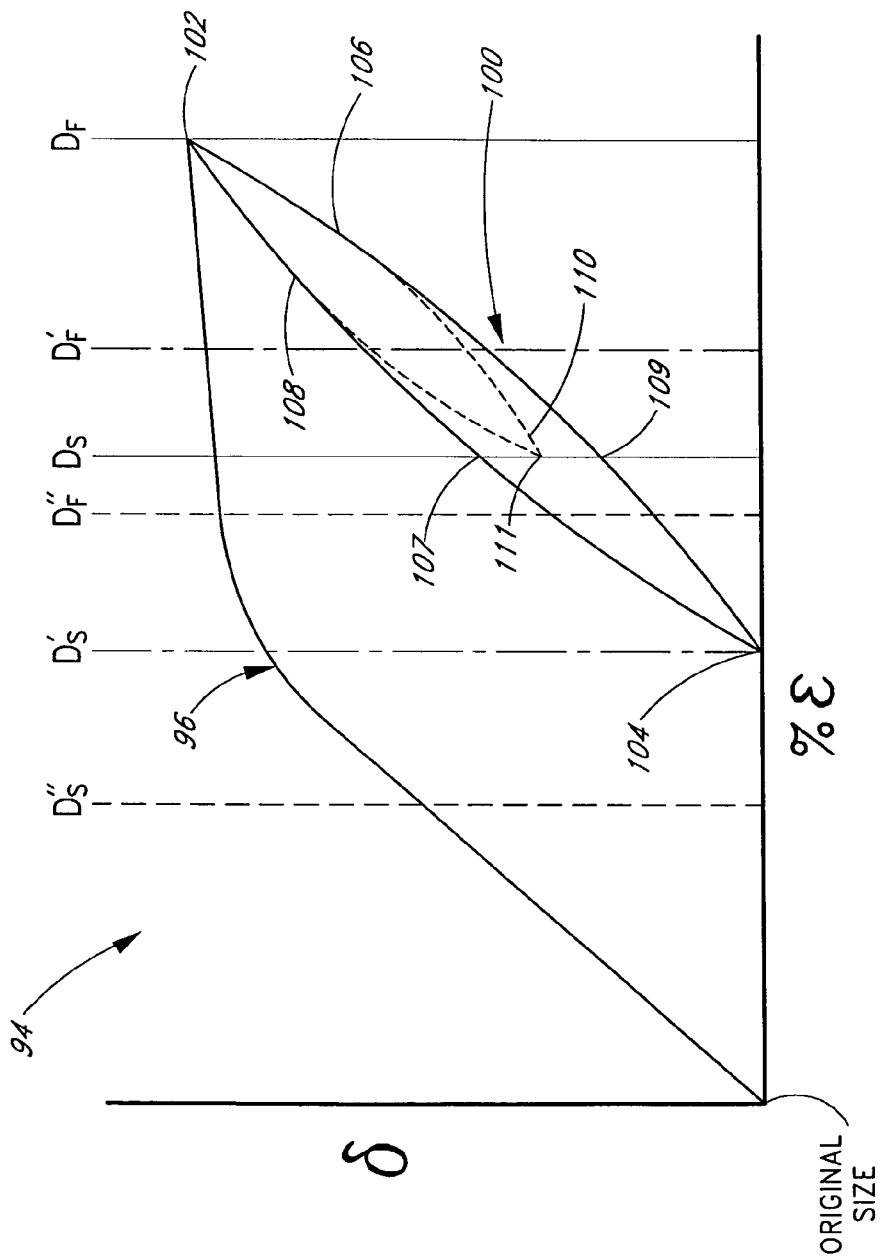
FIG. 12 illustrates another stress/strain curve generally representing the behavior of a material and schematically demonstrating deflection of a cardiac harness formed of the material.

With next reference to FIG. 12, another stress/strain curve 94 shows the behavior of stainless steel when it is deformed beyond its elastic limit. After plastic deformation has occurred, the material does not return to its original size, but it does recoil. A new elastic range 100 is established between the point of greatest deformation 102 and a point of maximum recoil 104. The material behaves in this newly established elastic range 100 substantially similarly as it behaves as discussed above with reference to FIG. 11. The newly-established elastic range 100 depicted in FIG. 12 also depicts a phenomenon often referred to as "hysteresis", in which, due to factors such as internal friction, a material follows a slightly different curve when being unloaded 106 than it does when being loaded 108. This type of behavior is common in materials, and is more pronounced in some materials than others.

The curve 94 of FIG. 12 can describe the behavior and stresses associated with a stainless steel cardiac harness that is constructed with a size and/or shape that is smaller than a patient's diseased heart. As the harness is installed on the patient's heart, it is plastically deformed to fit about the heart so that the point of greatest deformation 102 of the harness substantially matches the size and shape of the heart at the end of diastole $D_F$. In this manner, the stainless steel cardiac harness can be custom sized to fit the heart.

In the same manner as used in FIG. 11, the labels $D_S$ and $D_F$ identify the stress and strain associated with the size of the heart at the start and finish of diastole $D_S$, $D_F$, respectively, as the harness expands and contracts with the beating heart. Also as discussed above with reference to FIG. 11, the harness exerts a greater compressive force at the end of diastole $D_F$ than at the beginning of diastole $D_S$. As such, the greatest cardiac wall stress relief is provided at the end of diastole. During operation, the harness will expand and contract only between the sizes associated with the beginning and end of diastole $D_S$, $D_F$. Thus, only a portion of the new elastic range 100 between $D_S$ and $D_F$ is traversed by the harness material. This portion is depicted in FIG. 12 as a diastolic elastic range 110. As shown, due to the hysteresis phenomenon, the stress level 111 associated with the strain at $D_S$ is between the points 107, 109 on the loading and unloading curves 106, 108 of the new elastic range 100 of the deformed harness material.

Studies have indicated that relieving cardiac wall stress can significantly benefit a diseased heart, especially an enlarged heart. As wall stress is relieved, the heart muscle is better able to rest. Also, the pumping load on the heart is decreased significantly. Reducing wall stress in an enlarged heart will help stop and may even reverse enlarging, or remodeling of the heart. In this manner, the cardiac harness can function as a reshaping member, or reshaping harness, to help reshape or reverse remodel, a diseased heart.

As a heart reverse remodels, the size of the heart will tend to decrease; thus, the size of the heart at the beginning and end of diastole will change. For instance, in FIG. 12, an embodiment is presented wherein the enlarged heart whose size was originally represented by $D_S$ and $D_F$ reverse remodels and becomes smaller. The size of the smaller, reverse remodeled heart at the beginning and end of diastole is represented by $D'_S$ and $D'_F$, respectively.

As illustrated in FIG. 12, even for the reverse remodeled heart, the harness material still exhibits its greatest stress at the end of diastole $D'_F$, and thus the compressive force of the harness is greatest at the end of diastole $D'_F$. However, the magnitude of, the applied compressive force of the harness at both the beginning and end of diastole $D'_S$, $D'_F$ of the reverse remodeled heart is comparatively smaller than the magnitude of the compressive force applied to the heart before reverse remodeling (see $D_S$, $D_F$). In fact, in the embodiment shown, at the beginning of diastole $D'_S$ of the reverse-remodeled heart, there is substantially no force exerted by the harness.

With continued application of a compressive force to relieve cardiac wall stresses, it is anticipated that the heart will continue to reverse remodel and become even smaller still. As such, the size of an even further reverse remodeled heart at the beginning and end of diastole, represented in FIG. 12 as $D''_S$ and $D''_F$, is lesser still than previous measurements. In the illustrated embodiment, a compressive force is still exerted on the heart at the end of diastole $D''_F$, but substantially no force is exerted on the heart at the beginning of diastole $D''_S$. In fact, the heart no longer moves within the expansion range of the harness at the beginning of diastole $D''_S$. Thus, at the beginning of diastole $D''_S$, the heart is no longer within a deflection range of the harness wherein the harness exerts a positive compressive force on the heart.

Figure 12A:
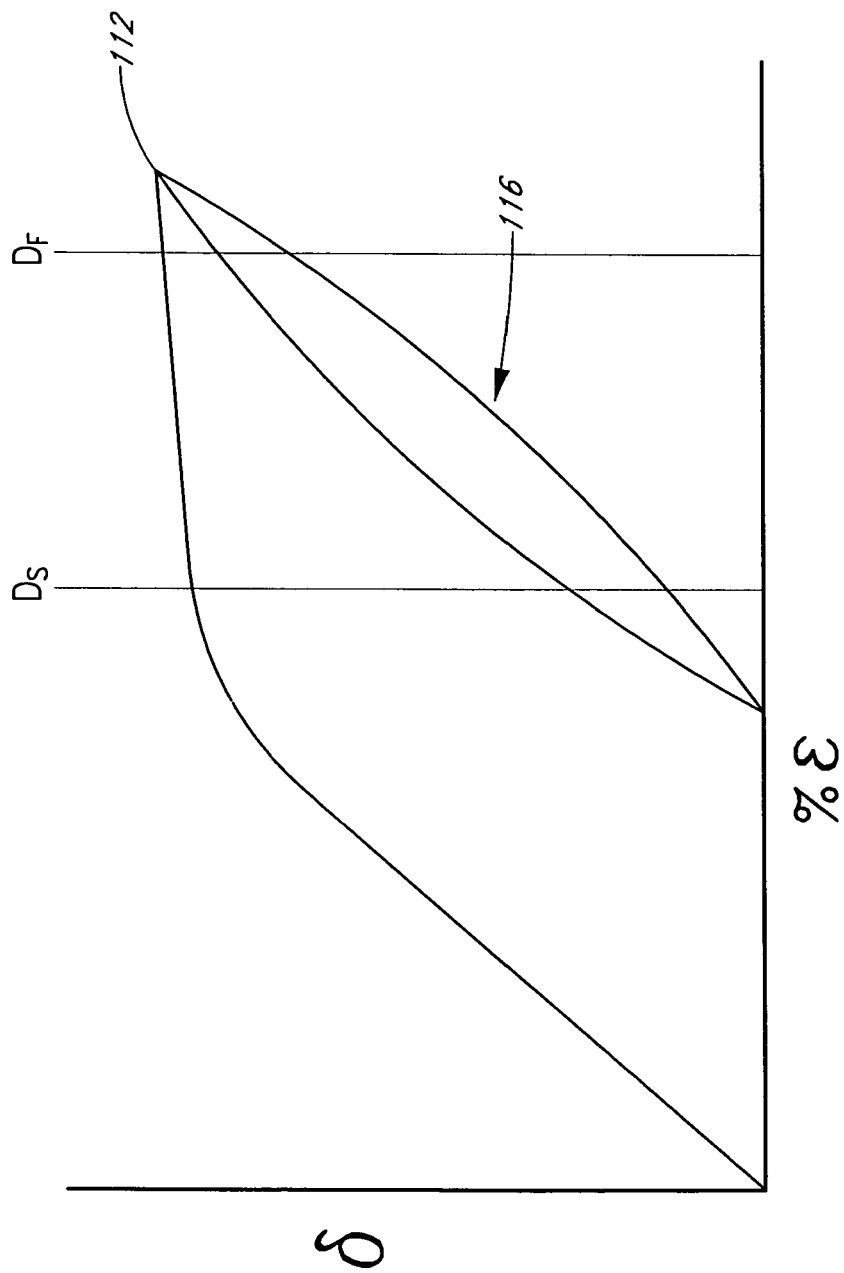
FIG. 12A illustrates the stress/strain curve of FIG. 12 and schematically demonstrates another embodiment of deflection of a cardiac harness.

With specific reference next to FIG. 12A, in accordance with another embodiment similar to the stainless steel cardiac harness of FIG. 12, rather than the harness being plastically deformed to substantially match the size of a diseased heart at the end of diastole $D_F$, the stainless steel harness can be stretched so that its point of maximum deformation 112 corresponds to a size or strain greater than the size of the diseased heart at the end of diastole $D_F$. In this embodiment, the harness is overstretched as it is installed on the heart. However, due to elastic recoil, the relaxed state of the harness is still smaller than the diseased heart. For example, and as shown, the harness still operates within an elastic recoil range 116 of the material such that a significant compressive force is exerted on the heart so as to relieve wall stresses. At the same time, however, the harness can be sized and arranged so that at the beginning of diastole $D_S$, substantially less compressive force is exerted on the heart wall.

In the embodiments discussed above, the cardiac harness has been shown to facilitate reverse remodeling of a heart. However, as the heart reverse remodels, the magnitude of the compressive force exerted by the harness becomes less and less, as shown in FIG. 12. Accordingly, the above embodiments may limit the extent a heart can reverse remodel.

In accordance with another embodiment, the cardiac harness can be constructed of a shape memory/superelastic material, such as one of the family of nickel titanium alloys known as Nitinol. Such a harness can be configured so that it is easily adjustable and can be repeatedly tightened about a patient's heart as the heart becomes smaller as a result of reverse remodeling. In this manner, the benefits of the mild compressive force exerted by the harness can be achieved over a wider range of heart sizes, and the degree of reverse remodeling of a heart will not be limited by the elastic range of the harness.

Nitinol is a material having structural and mechanical characteristics that are particularly suitable for cardiac harness applications. In order to appreciate these characteristics and to better describe embodiments comprising Nitinol, a basic understanding of the behavior of Nitinol alloys is helpful.

Nitinol exhibits transformational superelasticity, which refers to the ability of a material to reversibly transform a crystal structure upon the application of stress so that the material can undergo large elastic deformations without substantial plastic deformation. This type of superelasticity is exhibited when one crystal structure of the material transforms into another crystal structure. In Nitinol, a first crystal structure or phase is known as the austenitic phase, and a second crystal structure is known as the martensitic phase. In one state of the material, a Nitinol material is generally in a martensitic phase. In another state, a Nitinol material can be generally austenitic. In further states, a Nitinol material can be partially austenitic and partialy martensitic.

As discussed above, the family of Nitinol materials comprises various nickel titanium alloys. The alloys generally exhibit similar behaviors, although properties may vary somewhat between particular alloys. One property that is common among Nitinol alloys is that at relatively higher temperatures, Nitinol is at rest in the austenitic phase, and at relatively lower temperatures, Nitinol is at rest in the martensitic phase. More specifically, at temperatures above an austenite finish temperature $A_F$, unstrained Nitinol can be expected to be in the austenitic phase. The martensitic phase is not stable at such temperatures, and will automatically transform to the austenitic phase when the material exceeds an austenite finish temperature $A_F$. In practice, martensite transitions to austenite as the martensite is heated. The transition from martensite to austenite begins at an austenite start temperature $A_S$. At the austenite finish temperature $A_F$, the phase transformation is substantially complete, and relaxed Nitinol is substantially completely in the austentic phase.

Figure 13:
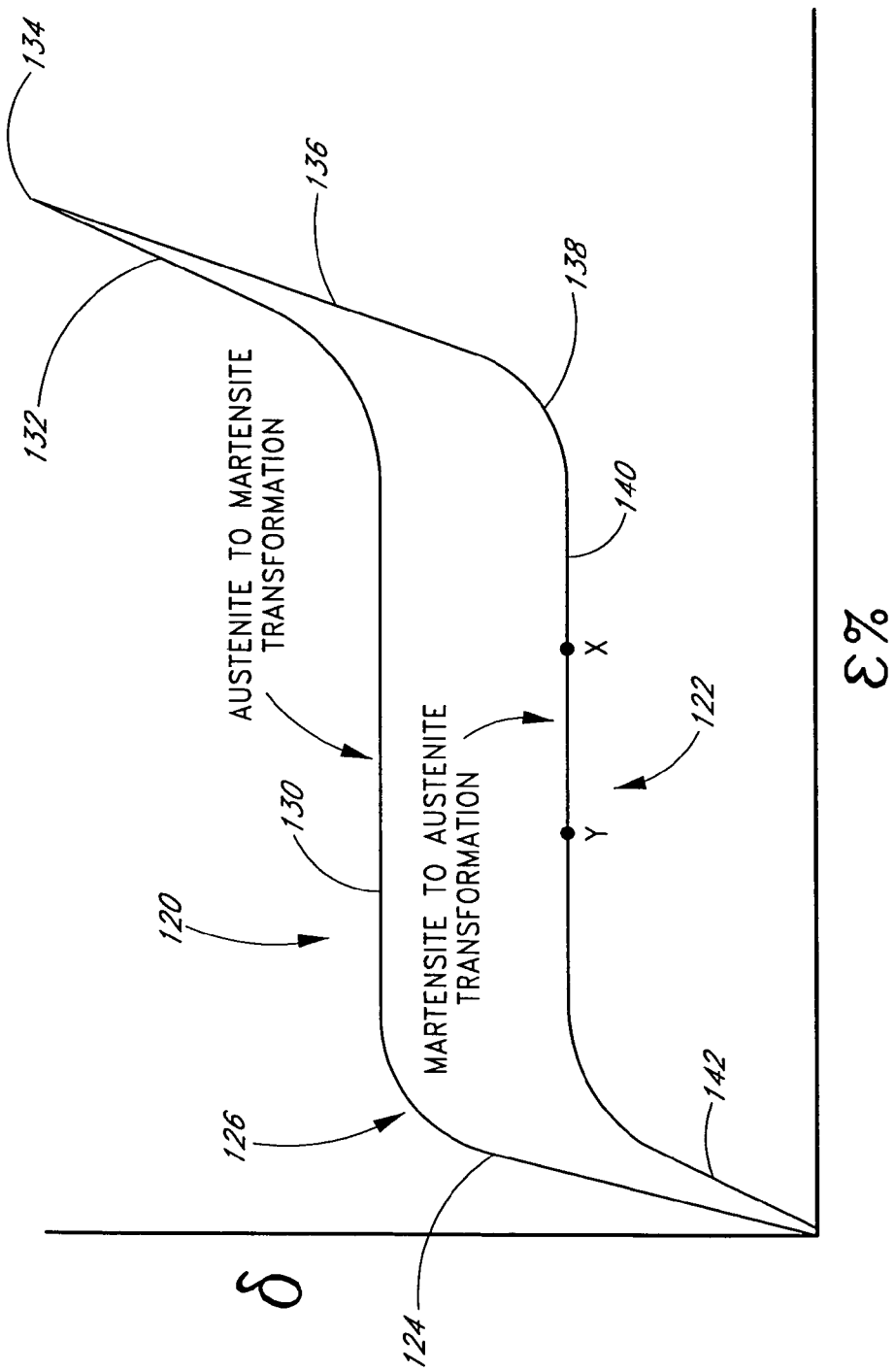
FIG. 13 shows an exemplary loading and unloading curve of Nitinol above an austenite finish temperature.

However, austenitic Nitinol can be transformed into martensitic Nitinol, even at temperatures above the finish temperature $A_F$, by inducing stress to the material. FIG. 13 shows an exemplary loading and unloading curve 120, 122 of Nitinol above the austenite finish temperature $A_F$. As discussed above, stable, relaxed Nitinol is in the austenitic phase at such temperatures. As a stress is applied, the austenitic Nitinol deforms elastically along a generally linear path 124 indicating its range of elastic deformation. At a critical yielding stress, the austenite begins to transform into martensite. During this transformation, the applied stress remains about the same, although there is a constant increase in the deformation of the material. Thus, the Nitinol forms generally a loading plateau 130 until the entire austenite phase transforms into the martensite phase. This condition of Nitinol is known as stress-induced martensite. After the transition from austenite to martensite is complete, the curve forms a generally linearly increasing path 132 corresponding to the range of martensitic elastic deformation. The curve terminates at a point of maximum elastic deformation 134.

As discussed above, martensite is unstable at temperatures above the austenite finish temperature $A_F$. When stress-induced martensite is unloaded, the material will automatically return to its austenitic phase along the unloading curve 122. With continued reference to FIG. 13, when the material is unloaded, it will first follow a linear path 136 as the martensitic phase elastically unloads. Note that due to factors such as internal friction, hysteresis occurs and there is not a substantial overlap of the loading and unloading curves 120, 122. At a second critical stress 138, the martensite begins to transform to austenite. In a manner similar to that observed during loading, the martensite-to-austenite transformation continues along a generally flat unloading plateau 140. When the martensite has completely transformed to austenite, the austenite material is elastically unloaded along another generally linear portion 142 of the unloading curve.

Figure 14:
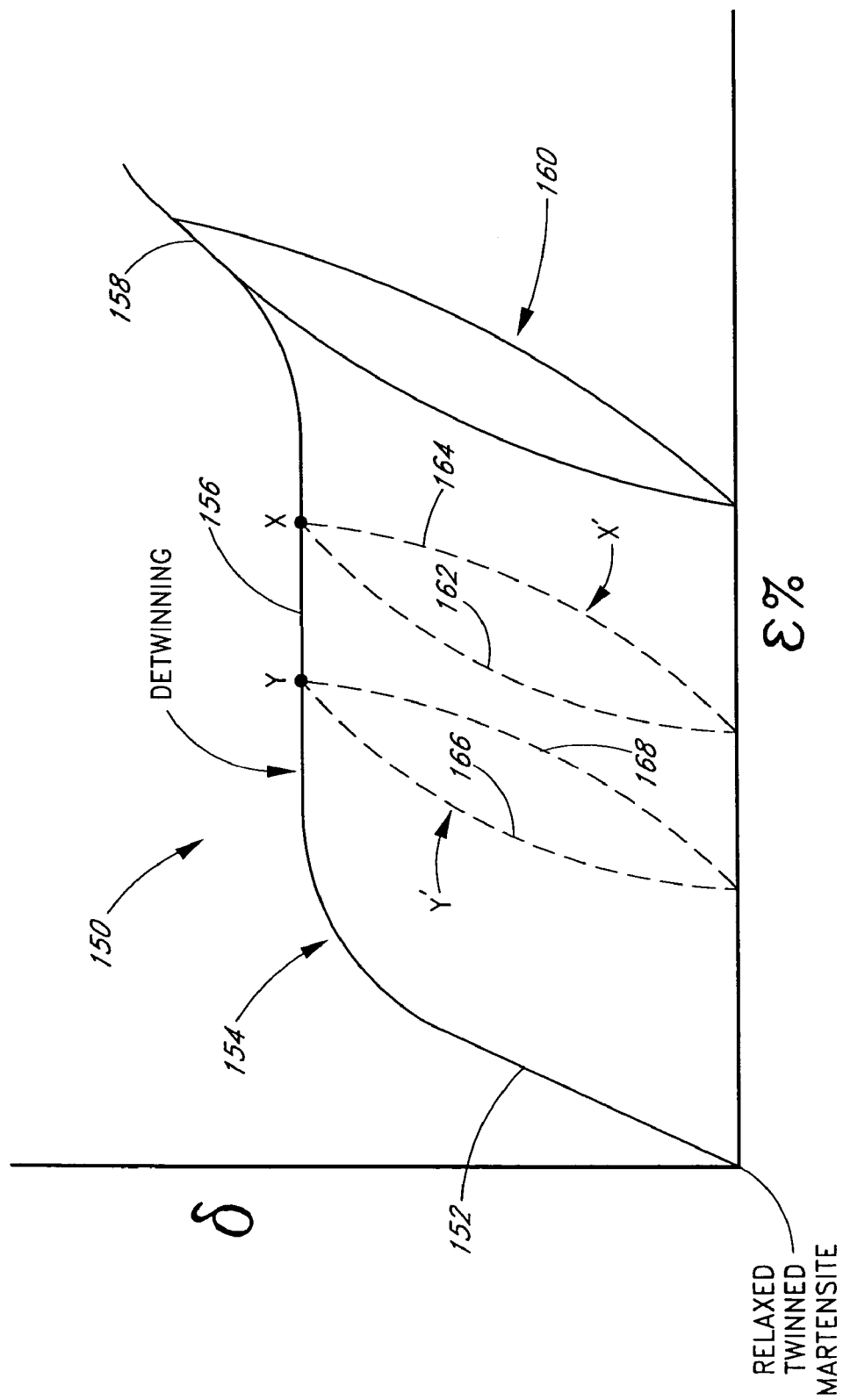
FIG. 14 illustrates a stress/strain curve of thermally-induced Nitinol.

FIG. 14 depicts a stress/strain curve 150 of a Nitinol material that has been annealed and then cooled to a temperature below a martensite finish temperature $M_F$. The austenitic phase is not stable at such temperatures. Austenitic Nitinol transforms into martensite as it is cooled through a range of temperatures. The transformation from austenite to martensite begins at a martensite start temperature $M_S$ and is substantially complete at the martensite finish temperature $M_F$. This phase of Nitinol is known as thermally-induced martensite and exhibits somewhat different behavior in response to applied stresses than austenitic Nitinol. As the Nitinol is cooled, it takes on a unique "twinned" crystal arrangement characteristic of thermally-induced martensitic Nitinol.

With continued reference to FIG. 14, as thermally-induced martensite is subjected to stress, the martensite first elastically deforms along a generally linear curve 152. At a critical stress value 154, the "twinned" arrangement of the martensitic crystals begins to be straightened out ("detwinning"). During detwinning, the martensitic Nitinol exhibits a generally flat loading plateau 156. Once the crystal structure has been detwinned, the martensitic Nitinol exhibits another substantially linear elastic deformation range 158. When the martensite is unloaded, it recoils elastically. However, the detwinned arrangement is retained, and the martensite will not automatically transform back into the twinned arrangement. Thus, as shown, the elastic recoil does not return along the loading curve 150 to the original size and shape of the thermally-induced Nitinol. Instead, the elastic recoil defines a new elastic range 160.

Once the martensite has been unloaded, it can be repeatedly elastically loaded and unloaded, but will remain within the new elastic deformation range 160, as shown in FIG. 14. Even partially detwinned thermally-induced martensite will not automatically transform back into a fully twinned arrangement. For example, if thermally-induced martensite is deformed to the deformation size X as set out on the loading curve of FIG. 14, the martensite has been only partially detwinned. If the material is then unloaded, the martensite will recoil, but will not retain. In fact, the Nitinol then has a new elastic range X' within which the Nitinol material can be repeatedly elastically loaded 162 and unloaded 164.

As discussed above, martensite is unstable at temperatures above the austenite finish temperature $A_F$, and will automatically begin to transform into austenite if subjected to temperatures above the austenite start temperature $A_S$. If thermally-induced martensite is heated to a temperature above the austenite finish temperature $A_F$, the martensite will spontaneously transform into austenite. However, if the material is under stress, or has been strained, it will behave like stress-induced martensite and will follow the generally flat unloading plateau 122 depicted in FIG. 13. For example, with simultaneous reference to both FIGS. 13 and 14, if the thermally-induced martensite which has been deformed to the point X in FIG. 14 is warmed to a temperature above the austenite finish temperature $A_F$, the martensitic material will transform into austenite and stress-induced martensite, and will begin to shrink from deformation size X toward deformation size Y along the unloading curve 122 depicted in FIG. 13. If, when the material has shrunken from size X to size Y, the material is then cooled to a temperature below the martensite finish temperature $M_F$, the Nitinol will return to the thermally-induced martensite phase and behavior depicted in FIG. 14, and will maintain the deformation size Y as an elastic limit as shown in FIG. 14. The Nitinol will also have a new elastic deformation range Y' in which the material can be repeatedly elastically loaded 166 and unloaded 168.

One way of controlling the shrinking of the Nitinol while at a temperature above the austenite transition temperature $A_F$ is to introduce an obstacle that prevents the Nitinol from shrinking beyond a certain size. For example, an obstacle may prevent the Nitinol device from shrinking beyond size Y in FIG. 13. Thus, if thermally-induced martensite of the size depicted at size X in FIG. 14 is heated to a temperature above the austenite transition temperature $A_F$ so that it follows the unloading curve 122 of FIG. 13 and becomes smaller, the material will cease shrinking at size Y because of the obstacle. The Nitinol material can then be cooled to a temperature below the martensite transition temperature $M_F$ so that the Nitinol is at size Y of FIG. 14, but is again in a thermally-induced martensite phase. In this manner, the elastic deformation range of thermally-induced martensite can be controllably shifted from a first range, such as X', to a second range, such as Y'.

The transition temperatures $A_S$, $A_F$, $M_S$, $M_F$ discussed above are partly a function of the particular Nitinol alloy employed and partly a function of the heat treatment to which the alloy is exposed. As such, through the use of known heat treatment methods, a Nitinol alloy can be customized to have austenite start and finish temperatures $A_S$, $A_F$ and martensite start and finish temperatures $M_S$, $M_F$ as desired for a particular Nitinol cardiac harness embodiment.

Further, throughout this specification, applicants employ a "functional" use of the transition temperatures $A_S$, $A_F$, $M_S$, $M_F$. Such a functional use is based upon the observed behavior of the Nitinol material in an embodiment of a cardiac harness rather than upon a molecular analysis of the material. For example, in this specification the functional austenite finish temperature $A_F$ is the temperature about at which the material begins to exhibit properties and behavior of substantially fully austenitic Nitinol. The functional austenite finish temperature $A_F$ does not necessarily require that 100% of the Nitinol, at a molecular level, is in the austenitic phase.

In a preferred embodiment, a cardiac harness is constructed of a Nitinol material having an austenite finish temperature $A_F$ above a normal human body temperature. Such a Nitinol material may be provided by using a particular alloy of Nitinol and/or by appropriately heat treating Nitinol in a known manner. The Nitinol harness of this embodiment preferably will be in a thermally-induced martensitic condition while inside the human body.

The thermally-induced martensitic Nitinol harness is sized so that when it is at rest it is substantially smaller than the diseased heart upon which it is to be placed. Additionally, the at rest size preferably is smaller than or about the same as a target heart size of the patient.

Figure 15:
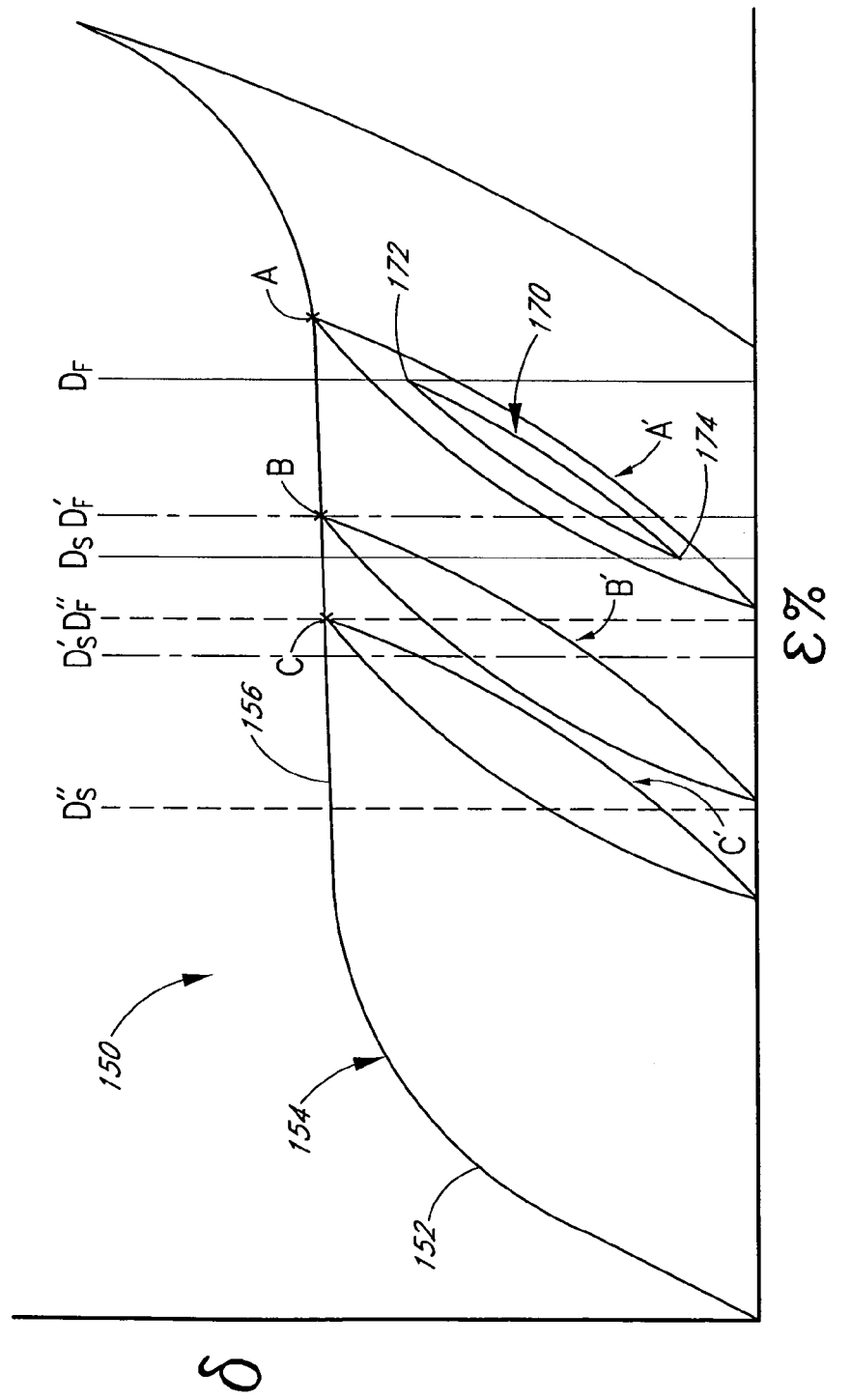
FIG. 15 illustrates a stress/strain curve of a thermally-induced Nitinol and depicts behavior of an embodiment of a cardiac harness taking advantage of the properties of Nitinol.

With next reference to FIG. 15, which includes a substantial reproduction of the thermally-induced martensite loading curve 150 of FIG. 14, as the harness is installed on the patient's heart, it is deformed generally along the expected deformation curve of thermally-induced martensite. The harness is stretched to be larger than the diseased heart upon which it is placed. For example, the point of greatest deformation A of the harness is somewhat beyond the point at which the heart would maximally deform the harness at the end of diastole $D_F$.

As can be seen in FIG. 15, when initially installed, the cardiac harness will have an elastic range as depicted by elastic range A'. As discussed above, the harness will operate within a diastolic elastic range 170 between the beginning and end of diastole $D_S$, and $D_F$. The compressive force associated with the stress 172 exerted by the harness at the end of diastole $D_F$ is substantially greater than the compressive force associated with the stress 174 exerted by the harness at the beginning of diastole $D_S$.

As also discussed above, application of the mild compressive force will tend to help the diseased heart reverse remodel so that the size of the heart will decrease, and correspondingly the size of the heart at the beginning and end of diastole decreases. In a similar manner as discussed in connection with FIG. 12 above, the labels $D'_S$, $D'_F$ in FIG. 15 represent the beginning and end of diastole of the reverse remodeled heart. As shown, when the heart has reverse remodeled, the compressive force exerted by the harness within elastic range A' at the beginning and end of diastole $D'_S$, $D'_F$ is decreased relative to the forces applied before reverse remodeling. The benefit provided by the harness is thus reduced, and further reverse remodeling may slow or stall.

In the illustrated embodiment, the Nitinol harness can be adjusted so as to move from the elastic deformation range A' to a new elastic deformation range B'. To adjust the harness, the temperature of the harness is increased above the austensite finish temperature $A_F$ of the Nitinol material. There are many ways to apply thermal energy to raise the temperature of a Nitinol reshaping harness. For example, application of electricity, warm liquids, etc., can raise the temperature as desired.

With continued reference to FIG. 15, in one preferred embodiment, the harness is bathed in a warm saline or water solution in order to adjust the harness from a first elastic range A' to a second elastic range B'. The warm liquid is supplied at a temperature above the finish temperature $A_F$, but below a temperature that would harm the body if the body is exposed to the temperature for a short period of time. The warm bath heats the Nitinol harness to a temperature above the austenite finish temperature $A_F$. The martensitic material will no longer be stable, and the harness will automatically begin transforming into an austenitic structure, exhibiting behavior as indicated on the unloading curve 122 of FIG. 13. The harness will shrink in size but will eventually be blocked from further shrinkage by the heart, which acts as an obstacle to prevent the harness from shrinking beyond the size of the reverse remodeled heart at about the end of diastole $D'_F$.

The warm liquid will soon disperse or cool to body temperature, which preferably is below the martensite transition temperature $M_F$. Thus, the Nitinol harness will resume its thermally-induced martensitic structure and will again exhibit behavior along the curve 150 of FIG. 15. However, the harness will have shrunk so as to fit snugly around the heart. The harness will have a maximum size as indicated at point B, and an elastic deformation range resembling range B'. As such, the compressive force exerted by the harness at the end of diastole $D'_F$ is at or above the level of force when the harness was initially installed in the patient. This level of compressive force is beneficial and will initiate further reverse remodeling of the heart.

As time passes and the heart further reverse remodels, the heart will become yet smaller still. Eventually, as happened previously when the harness was operating in elastic range A', the size of the further reverse remodeled heart at the beginning and end of diastole (now labeled $D''_S$, $D''_F$) will be such that the harness, when operating in elastic range B', no longer helps the heart further reverse remodel. At or near such time, the procedure described above, wherein the harness is warmed to a temperature above the austenite finish temperature $A_F$ so that the harness shrinks to the current size of the heart, and then cools back below the martensite finish temperature $M_F$, is repeated. The harness is again fit snugly about the heart and the elastic range shifts from range B' to a new range C'.

As can be appreciated, the adjustment process can be repeated as often as desired or until the heart has reverse remodeled to a point at which the patient and clinician are satisfied with the results. This process can also be controlled so that the heart reverse remodels to a target heart size. The harness can be configured and manipulated to exert substantially no compressive force at the beginning of diastole when the heart has reached its target size.

As shown in FIG. 15, when the harness shifts between elastic ranges, such as when the harness shifts from elastic range A' to elastic range B', the range of stresses available within the elastic ranges A', B' remain generally the same. However, the strain range, or deflection range, of the harness shifts. As such, in the new elastic range, the harness can provide the same or similar reshaping forces to the heart, but the size of the harness has changed. Thus, substantially similar reshaping forces can be applied to a progressively smaller-sized heart.

This principle is especially beneficial in improving the safety of the harness, because the maximum reshaping force of the ranges remains substantially the same over the working range of the harness, even though the size of the harness can change. As such, the harness preferably is sized and configured so that the maximum reshaping force does not exceed a predetermined value during use of the device. For example, in one embodiment, a cardiac harness is sized and configured relative to the diseased heart to be treated so that the compressive force exerted by the harness on the heart will never exceed about 20 mmHg. In another embodiment, the compressive force limit can be about 15-17 mmHg.

The above-described harness embodiments are relatively easy to install and adjust. Minimally invasive methods can be used to install the Nitinol harness around the heart. Additionally, the clinician need not worry excessively about deforming the harness unevenly or sizing the harness imprecisely when installing the apparatus around the heart. This is because even if the apparatus is somewhat larger than the heart, the apparatus will operate in a range of elasticity which will include the size and shape of the heart. Besides, the harness can be easily adjusted at any time as discussed above so as to fit snugly around the heart.

In an additional embodiment, during installation, the clinician stretches the harness during installation so that the harness it is larger than the heart. This allows the clinician to install the harness minimally invasively and with relatively little need to avoid deforming the harness to be larger than the heart. After the harness is wrapped, perhaps loosely, around the heart, the clinician bathes the heart and harness in a warm liquid having a temperature above the austenite finish temperature $A_F$ of the harness. In a manner as described above, the harness will shrink to substantially conform to the size and shape of the heart. As the liquid cools to body temperature, the harness again cools to a thermally-induced martensite structure and operates in an anticipated elastic range. As such, the clinician needs only very little precision in installing the harness over the heart, yet the harness will be shaped to match and hug the heart once installed.

In a further additional embodiment of a method for installing and using embodiments of the harness, after installation of the harness on the patient's heart, the patient's pericardium is substantially closed by the clinician. With the pericardium substantially closed, the heart can be bathed in a warm saline or water solution by simply injecting the warm liquid into the space between the pericardium and the heart. The warm liquid will be held in that space, and thus will be able to substantially evenly heat the harness to a temperature above the austenite finish temperature $A_F$. The clinician may allow the warm liquid to cool and then naturally disperse from the pericardium, or the clinician can suck the warm liquid out of the pericardium by using the same medium used to deliver the liquid. Even if the pericardium is not substantially closed by the clinician, the heart and harness still can be bathed in warm water in order to heat the harness as desired.

As discussed above, the process of warming the harness so that it adjusts itself snugly about the patient's heart can be repeatedly performed in order to accommodate and encourage reverse remodeling. Preferably, the repeated adjustments are performed by injecting warm liquid between the closed pericardium and the heart, as just discussed. This operation can be conveniently and safely performed by a surgical procedure such as a procedure similar to the well known pericardiocentesis procedure.

Figure 16:
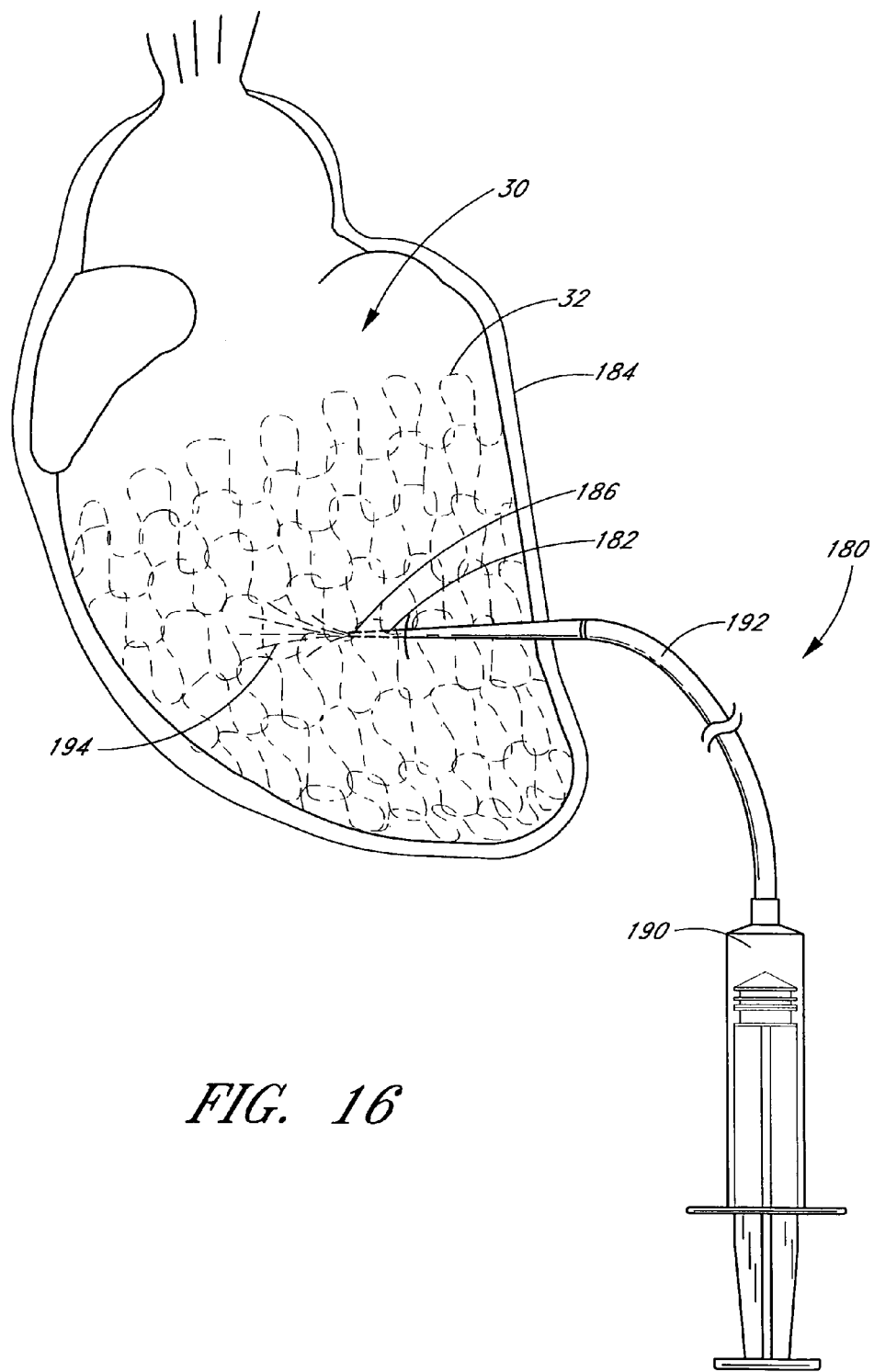
FIG. 16 depicts a method and apparatus for injecting a warm fluid between a pericardium and heart wall.

With next reference to FIG. 16, a procedure for warming the harness is illustrated schematically. A clinician employs an apparatus 180 having a needle-like tip 182 to penetrate the patient's tissue, including the pericardium 184. The open distal end 186 of the tip 182 is arranged between the pericardium 184 and the heart 30 outer wall. A source of warm fluid, such as a syringe 190, communicates with the needle 182 through a tube 192, and warm fluid 194 is supplied from the source 190 into the space between the pericardium 184 and the heart 30. After the fluid 194 has warmed the harness 32 in order to adjust the size of the harness, the clinician draws back the syringe 190 to retract at least some of the fluid. Alternatively, the fluid may be left in place to be naturally disposed of by the body. This exercise may be carried out once or, to ensure coverage of substantially the entire harness, warm fluid can be introduce at several points about the heart.

Figure 17:
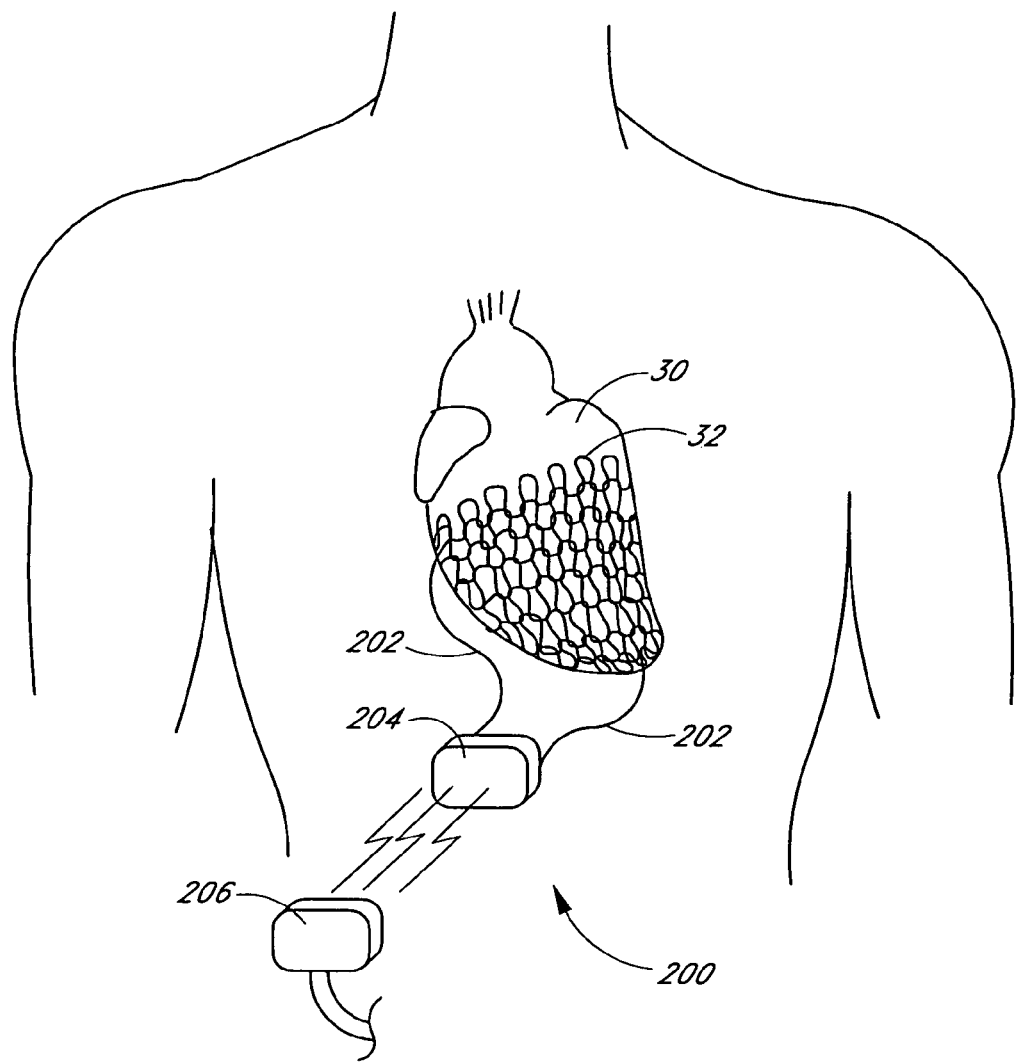
FIG. 17 depicts a method and apparatus for electrically warming and adjusting a cardiac harness disposed on a heart.

With next reference to FIG. 17, another embodiment of a method and apparatus 200 for warming and adjusting the harness is illustrated. In the illustrated embodiment, at least two wire leads 202 are connected to the harness 32. An internal controller 204 is placed within the patient's body and controls the flow of electricity to the leads 202. An external radio controller 206 can be used to actuate and energize the internal controller 204. In accordance with one embodiment, application of a voltage difference between the wire leads 202 will create a current through the harness 32, which current warms the harness to a desired temperature sufficient to urge the harness to adjust. The voltage preferably is chosen to not significantly interrupt the electrical stimulation of the heart's own electrical system during pumping.

In the illustrated embodiment, two wire leads 202 are disposed on the harness 32, one near the base 52 of the harness and the other near the apex 56. In an additional embodiment, several wire leads are provided, and the internal controller selectively actuates the leads in accordance with a control system so that only certain pairs of leads are actuated at any one time. As such, the internal controller controls how the harness is adjusted on the heart. For instance, in one embodiment, leads near the base of the heart are actuated before leads near the apex. As such, the size of the harness 32 is adjusted from the base 52 towards the apex 56. This helps maintain the position of the harness upon the heart, because if the harness were made tighter about the apex than it is about the base, there may be an increased tendency for the harness to be pulled toward the base, and the fit of the harness 32 on the heart 30 may be compromised.

In embodiments discussed above, the behavior of the Nitinol cardiac harness has been depicted as movable between the curves of FIGS. 13 and 15 in response to application of thermal energy. The discussed embodiments describe raising the temperature of the Nitinol above the austenite finish temperature $A_F$ to obtain behavior along the curve of FIG. 13, and then lowering the temperature of the Nitinol below the martensite finish temperature $M_F$ to obtain behavior along the curve of FIG. 15. In an additional embodiment, a thermally-induced martensite cardiac harness is adjusted by raising the temperature of the harness above the austenite start temperature $A_S$, without necessarily raising the temperature above the finish temperature $A_F$. In this manner, at least some of the martensitic Nitinol transforms to austenite, and the harness will begin to adjust.

In a still further additional embodiment, a Nitinol cardiac harness is provided having an austenite start temperature that is less than a patient's normal body temperature, about 37° C. As such, the harness is partially austenitic during normal operation within a patient's body, and will exhibit characteristics of both austenite and thermally-induced martensite.

Figure 18:
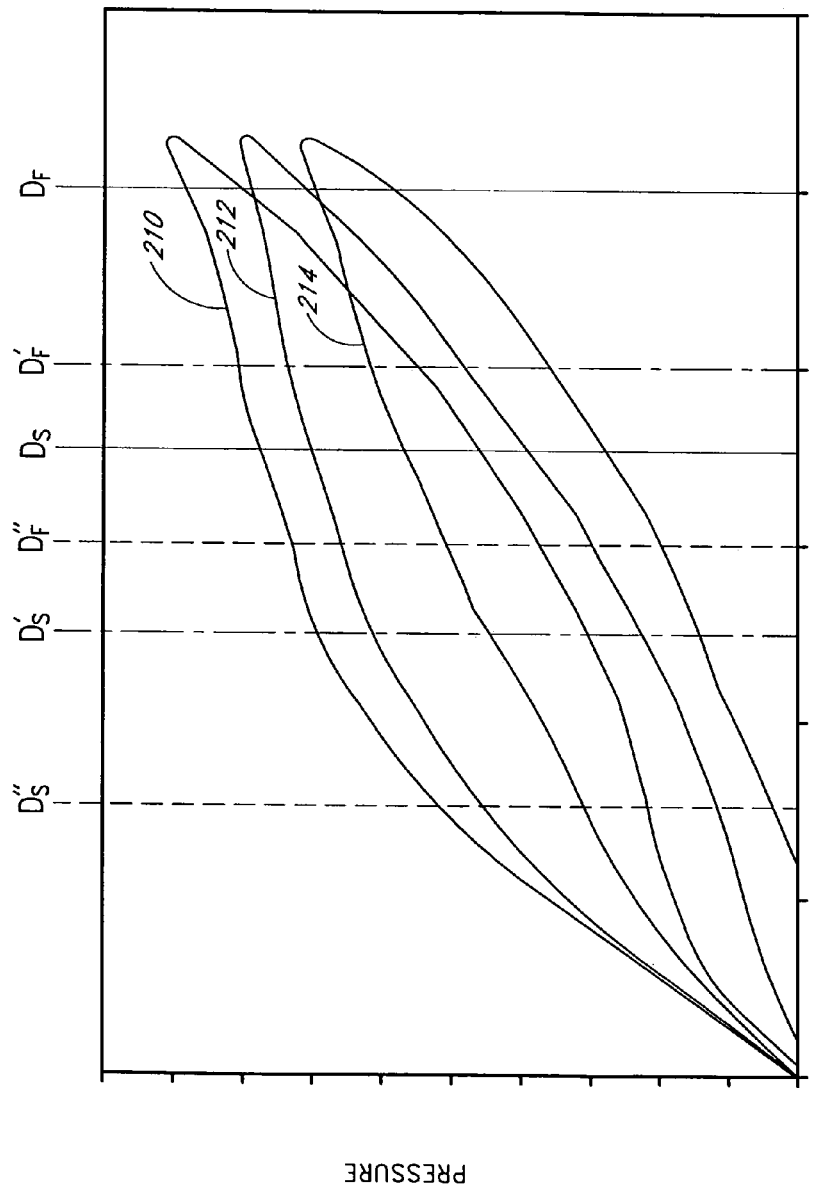
FIG. 18 shows a series of curves representing test data for an embodiment of a cardiac harness.

With next reference to FIG. 18, a series of curves 210, 212, 214 represents test data for an embodiment of a Nitinol harness. Each curve plots a pressure exerted by the harness in response to a corresponding deformation of the harness. Each of the three curves 210, 212, 214 represents the deformation behavior of the harness at a specified temperature $T_1$, $T_2$, $T_3$, respectively. As shown, each curve 210, 212, 214 has a generally similar shape, and has a relatively low increase in pressure exerted over a relatively wide range of deformation. The curve shapes are attributable to the design of the harness and to the characteristics of the Nitinol material.

In FIG. 18, the curve 210 taken at the highest temperature $T_1$ exerts the greatest magnitude of pressure. As discussed above, an increase in temperature above $A_S$ prompts an increase in the proportion of Nitinol that is austenitic. Austenitic Nitinol tends to be more resistant to deformation than martensitic Nitinol. Thus, since the proportion of austenite in the harness increases with increasing temperature, the magnitude of pressure applied by the harness with increasing temperature also increases. Accordingly, in a further embodiment, a Nitinol cardiac harness has austenite start and finish temperatures $A_S$, $A_F$, configured so that the proportion of austenite to martensite at a patient's body temperature is such that the harness applies a pressure to the heart within a desired therapeutic range.

An applied pressure within a therapeutic range is defined herein as a pressure of sufficient magnitude that, when applied to an organ such as the heart, results in a benefit to the organ. In one embodiment, the therapeutic range for a cardiac harness is between about 5-20 mmHg. More preferably, the therapeutic pressure is about 7-15 mmHg.

In another embodiment of a Nitinol cardiac harness, the harness is treated to have an austenite start temperature $A_S$ below room temperature, about 30-33° C. As such, the stiffening properties of austenite help the harness to hug the heart even if the harness and heart are exposed to relatively-low room temperatures during harness installation. Of course, when installation is complete and the harness warms to the patient's body temperature, the proportion of austenite rises, and the pressure exerted by the harness will correspondingly rise. In a still further embodiment, a harness having an $A_S$ below room temperature has an austenite finish temperature $A_F$ below body temperature so that the harness is substantially fully austenitic during operation. Alternatively, the $A_F$ remains above body temperature so that the harness remains at least partially martensitic.

With continued reference to FIG. 18, and in a manner as discussed above with reference to FIGS. 12-15, labels $D_S$ and $D_F$ have been applied to illustrate the relative pressures applied by the harness at the beginning and end of diastole. As also discussed above, as a heart reverse remodels, the size of the heart generally decreases, as indicated by $D'_S$ and $D'_F$. Further reverse remodeling is represented by $D''_S$ and $D''_F$. Although the pressure exerted by the harness at the end of diastole $D_F$, $D'_F$, $D''_F$, may decrease as the heart reverse remodels, the applied pressure remains within a desired therapeutic range. Thus, a cardiac harness is configured to adjust continuously with the heart as the heart changes in size and continuously provides a therapeutic applied pressure to a patient's heart even when the patient's heart reverse remodels extensively.

Figure 19:
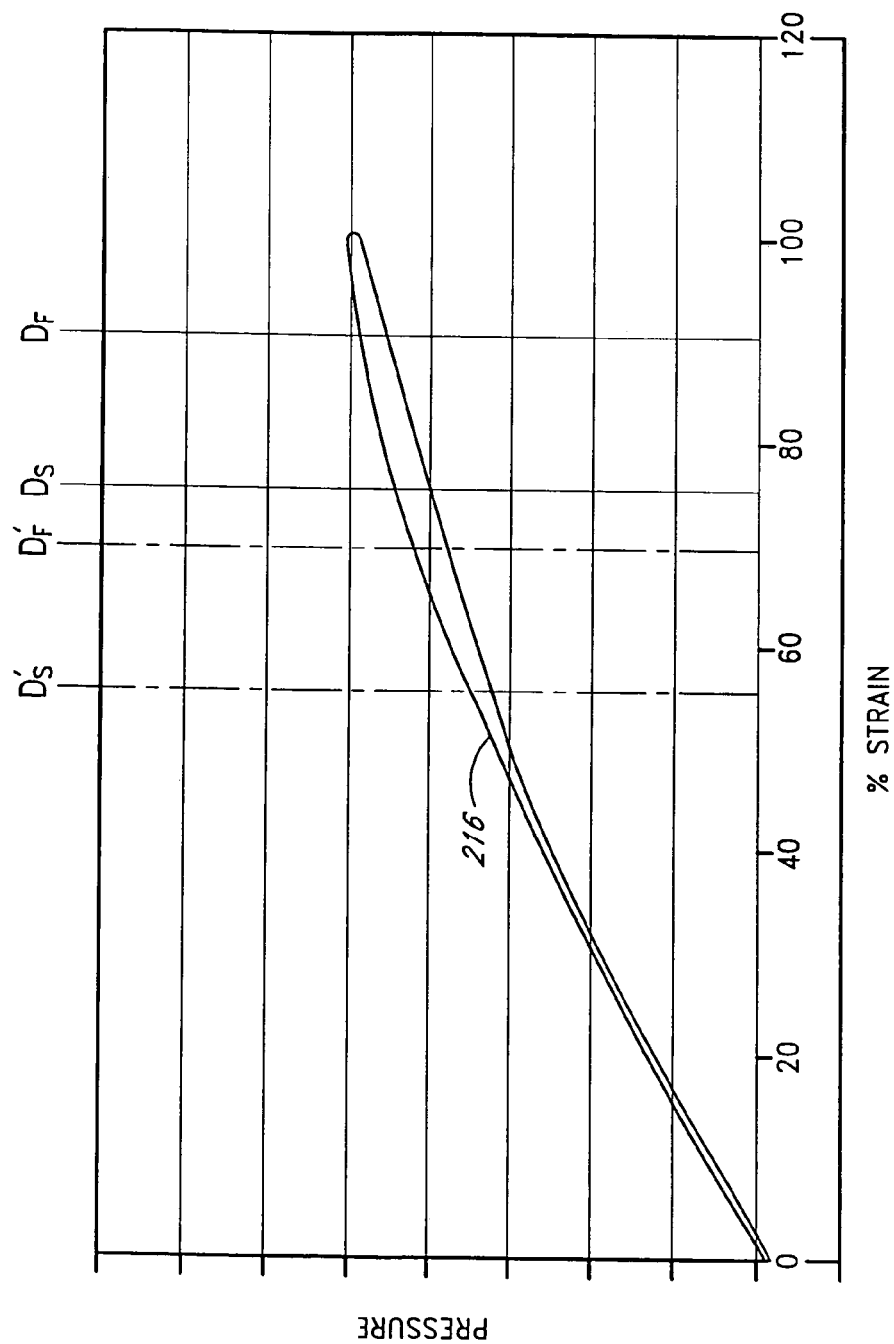
FIG. 19 shows a curve representing test data for another embodiment of a cardiac harness.

With next reference to FIG. 19, a pressure versus percentage strain curve 216 is presented for an embodiment of a Nitinol cardiac harness having an austenite finish temperature $A_F$ lower than room temperature. In this embodiment, the harness is substantially fully austenitic before and during installation, although at least some stress-induced martensite may form during harness deformation. In a manner as discussed above, the labels $D_S$, $D_F$, $D'_S$, and $D'_F$ illustrate the relative pressures applied by the harness at the beginning and end of diastole as the heart reverse remodels. In the illustrated embodiment, the cardiac harness adjusts continuously with the heart as the heart changes in size, and also applies a therapeutic pressure to the heart even when the heart reverse remodels extensively.

In accordance with embodiments discussed above, the cardiac harness is deformed from an at-rest, unstretched size and shape to a stretched configuration in order to be installed on a patient's heart and apply a therapeutic pressure thereon. In such embodiments, the harness can be extensively deformed from its at-rest size and shape. In accordance with one embodiment, the unstretched size of the harness is about 25-70% of the size of the enlarged heart to be treated. More preferably, the at rest size of the harness is about 30-50% of the size of the enlarged heart to be treated.

The principles discussed above can be applied to any number of other embodiments. Such embodiments can comprise modifications of the embodiments discussed above or can comprise totally different products. More specifically, aspects of the cardiac harness embodiments discussed above can be applied to other types of apparatus for reshaping organs. As such, various reshaping harnesses or reshaping devices can apply aspects of the above-discussed cardiac harness embodiments for other uses and organs.

As a patient's heart enlarges during congestive heart failure, the annulus of certain valves, such as the mitral valve, tends to grow with the heart. Eventually, the valve annulus may increase in size to a point at which the leaflets are not large enough to completely close the valve. Another factor contributing to valve dysfunction is that as the heart enlarges, the geometry of the heart changes somewhat. Portions of the heart such as the papillary muscles are moved outwardly from the leaflets to which the papillary muscles are attached via the chordae tendinaea. These papillary muscles may be stretched to their limit so that they prevent the valve leaflets from adequately approximating each other. As such, the leaflets will not be able to fully close, and the valve will leak; such valve leakage simply makes the patient's heart problems worse.

In accordance with another embodiment, a harness or collar comprising one or more rows of undulating springs/hinges can be configured to exert a compressive force on specific portions of a heart so as to help prevent or diminish valve dysfunction. For example, a collar-type device comprising one or more undulating hinges can be specially configured to fit around a region of the heart known as the AV groove. The AV groove is generally adjacent the mitral and tricuspid valves of the heart. An AV groove collar can be arranged and configured according to the principles discussed in this application so as to exert a compressive force that will tend to decrease the size of the valvular annuli and/or prevent enlargement of the valvular annuli beyond a desired size.

In another embodiment, a papillary muscle band can be provided, comprising a plurality of undulating springs/hinges specifically sized and configured to be placed around the heart in the area of the papillary muscles. As known in the art, the papillary muscles are generally midway between the AV groove and the apex of the heart. Thus, a papillary muscle band can. exert a compressive force to reduce the diameter of the heart at the level of the papillary muscles. This will help the papillary muscles become less stretched so that they do not prevent closure of the valve leaflets.

As discussed above, a cardiac harness applies a mild compressive force on a patient's heart. It is anticipated that embodiments of an AV groove collar and papillary muscle band will exert a more aggressive compressive force than a typical cardiac harness. It is also anticipated that the AV groove collar and papillary muscle band can be used independent of one another or in conjunction with one another and either independent of or in conjunction with a cardiac harness. For example, a papillary muscle band can be placed on the heart before or after installation of a cardiac harness.

In still further embodiments, portions of a cardiac harness can be provided with varying stiffness, and an AV groove collar and papillary band can be incorporated into a cardiac harness so as to apply specially-directed forces to the specific portions of the heart.

Embodiments of an AV groove collar and papillary muscle band can be manufactured of Nitinol or other shape memory material. As such, these devices can be placed upon a heart without worrying about fitting the devices too closely. Applying heat will then shrink the devices so that they fit snugly about the respective portions of the heart. Additionally, these devices can be adjusted after the initial installation so as to prolong the beneficial effect anticipated by such devices.

In accordance with still further embodiments, reshaping harnesses made of material such as Nitinol can be used to change the shape or affect the function of various organs within the body, and can be adjusted in place so as to apply a reshaping force on those organs.

It is not uncommon for certain relatively obese patients to undergo a procedure known as stomach stapling. In this procedure, the size of the stomach is reduced so as to correspondingly reduce the appetite and food intake of the patient. In another embodiment having aspects of the present invention, a stomach harness or gastric band can be provided that is configured to fit substantially around at least a portion of a patient's stomach. The harness applies a compressive force on the stomach so as to substantially restrict the size of the stomach. The device can be installed relatively loosely around the stomach and then be heated briefly so as to shrink the device tightly about the stomach. The device will then exert a force on the stomach that will tend to reduce the stomach size and reduce the patient's appetite. Of course, this device can later be tightened again and again by repeatedly supplying heat to the device.

Yet another advantageous embodiment of the device is used to treat aneurysms in various regions of the body such as, for example, in the brain, a ventricle, or the aorta. Such aneurysms often contain clotting blood or the like and it is not necessarily advantageous to completely and suddenly reshape the aneurysm or return it to its original shape. In contrast, it may be preferable to slowly urge the aneurysm back to its original and intended shape. A harness-type band can be installed about the aneurysm and configured and adjusted to fit snugly over the aneurysm, while exerting a mild compressive force thereon. As time passes, the aneurysm will be slowly reshaped. If necessary, the compressive band can also be adjusted in a manner as described above. As such, a flexible Nitinol band can controllably and safely treat an aneurysm.

In still another embodiment, a Nitinol harness can be useful in retinal surgery. It is common in retinal surgery to apply a scleral band or scleral buckle about a patient's eyeball at the completion of the surgery. In one embodiment, a ring-shaped scleral band is preferably constructed of Nitinol having an austenite finish temperature $A_F$ below normal body temperature. Thus, the band can be expanded to be easily placed around the patient's eyeball, and will automatically constrict to hold itself snugly on the eyeball. In another embodiment, the scleral band is constructed of Nitinol having an austenite finish temperature $A_F$ above human body temperature. Thus, a clinician can deform the band to fit it over the patient's eye and then can apply heat so that the band shrinks down to the size of the eye. After the band cools to the thermally-induced martensite condition, it will exert a mild compressive force on the eye, but will be still be relatively flexible.

In still further embodiments, a Nitinol reshaping harness can be used in other applications such as, for example, compression bandages, which help reduce swelling immediately after surgery.

Although the embodiments discussed above have been discussed specifically in light of Nitinol, it is to be understood that various other materials can be used for a cardiac harness and can employ some or all of the aspects discussed herein. For example, non-Nitinol superelastic and/or shape memory materials can exhibit properties and behavior that is similar to, if not the same as, at least some of the aspects of Nitinol as discussed above. For example, other materials exhibit transformational superlasticity. Some suitable cardiac harness materials can include metals and polymers such as oligo (e-caprolactone), dimethacrylate, Elgiloy™, titanium and tantalum.

The devices in the above embodiments have been described as comprising a plurality of hinges or spring elements. It should be understood, however, that a variety of configurations and arrangements that allow the harness to expand and contract would be acceptable. For example, in other embodiments, a harness-type device can be constructed of expandable, braided filaments. Such embodiments can be constructed of a variety of materials, but, if shape memory/superelastic materials such as Nitinol are used, these devices can take advantage of the principles and characteristics described above.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A cardiac harness for treating a heart, comprising:
   a cardiac harness formed from nitinol material and having a premounted size, wherein the premounted size harness is at rest, and a mounted size, wherein the mounted size harness is elastically deformed from the premounted size harness and applies a therapeutic compressive force on the heart; and
   the cardiac harness premounted size being about 25% to about 70% smaller than the mounted size.

2. The cardiac harness of claim 1, wherein the cardiac harness premounted size is an at-rest, unstretched configuration.

3. The cardiac harness of claim 2, wherein the cardiac harness is elastically deformed as it is being mounted on the heart.

4. The cardiac harness of claim 3, wherein the cardiac harness is configured to apply continuous compressive force on the heart during both diastole and systole.

5. The cardiac harness of claim 4, wherein the cardiac harness applies a peak compressive force on the heart in the range of about 5 mm Hg to about 20 mm Hg.

6. The cardiac harness of claim 1, wherein the cardiac harness is configured for minimally invasive delivery.

7. The cardiac harness of claim 6, wherein the cardiac harness is elastically deformed as the harness is mounted on the heart so that the harness automatically applies a compressive force on the heart.

8. A cardiac harness for treating a diseased heart, comprising:
   a cardiac harness formed from nitinol material and having a premounted size and a mounted size;
   the cardiac harness premounted size being about 25% to about 70% less than the size of the heart prior to the harness being mounted on the heart; and
   the cardiac harness being configured so that the harness is elastically deformed as the harness is mounted on the heart thereby automatically applying a compressive force on the heart that does not exceed 20 mm Hg.

9. The cardiac harness of claim 8, wherein the nitinol material is in a thermally-induced martensitic phase.

10. The cardiac harness of claim 8, wherein the cardiac harness applies a peak compressive force on the heart in a range of about 5 mm Hg to about 20 mm Hg.

11. The cardiac harness of claim 10, wherein the compressive force exerted by the cardiac harness at the end of diastole $D_F$ is greater than the compressive force exerted by the harness at the beginning of diastole $D_S$.

12. The cardiac harness of claim 8, wherein the cardiac harness is configured for minimally invasive delivery.

* * * * *

UNITED STATES PATENT AND TRADEMARK OFFICE
CERTIFICATE OF CORRECTION

PATENT NO.        : 7,404,793 B2                                   Page 1 of 1
APPLICATION NO.   : 10/837157
DATED             : July 29, 2008
INVENTOR(S)       : Lilip Lau et al.

It is certified that error appears in the above-identified patent and that said Letters Patent is hereby corrected as shown below:

Title Page, Related U.S. Application Data,
Item (63), insert --Continuation of application No. 10/287,723, filed on Oct. 31, 2002, now Pat. No. 7,276,021--.
Item (60), insert --Provisional application No. 60/335,437, filed on Oct. 31, 2001--.

Page 4, OTHER PUBLICATIONS,
Column 1, after "Doty, Donald B., et al., Septation of" delete "teh" and insert --the--.
Column 1, after "Schetky, L. McDonald," delete "*Shap- Memory Alloys*" and insert --*Shape Memory Alloys*--.

Column 7,
Line 19, delete "strain 6" and insert --strain å--.

Column 10,
Line 63, delete "retain" and insert --retwin--.

Column 14,
Line 53, delete "introduce" and insert --introduced--.

Column 17,
Line 33, delete "band can. exert" and insert --band can exert--.

Signed and Sealed this

Ninth Day of December, 2008

JON W. DUDAS
*Director of the United States Patent and Trademark Office*